(12) United States Patent
Maeda

(10) Patent No.: US 10,849,583 B2
(45) Date of Patent: Dec. 1, 2020

(54) MEDICAL IMAGE DIAGNOSTIC APPARATUS AND MEDICAL IMAGE PROCESSING APPARATUS

(71) Applicant: Toshiba Medical Systems Corporation, Otawara (JP)

(72) Inventor: Tatsuo Maeda, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 229 days.

(21) Appl. No.: 15/700,827

(22) Filed: Sep. 11, 2017

(65) Prior Publication Data

US 2018/0070903 A1  Mar. 15, 2018

(30) Foreign Application Priority Data

Sep. 12, 2016  (JP) ................. 2016-177981

(51) Int. Cl.
*G06K 9/00* (2006.01)
*A61B 6/00* (2006.01)
(Continued)

(52) U.S. Cl.
CPC .............. *A61B 6/504* (2013.01); *A61B 6/06* (2013.01); *A61B 6/461* (2013.01); *A61B 6/5205* (2013.01);
(Continued)

(58) Field of Classification Search
CPC ......... A61B 6/06; A61B 6/4441; A61B 6/461; A61B 6/481; A61B 6/504; A61B 6/5205;
(Continued)

(56) References Cited

U.S. PATENT DOCUMENTS

2005/0256389 A1   11/2005  Koga et al.
2010/0231605 A1    9/2010  Moriya et al.
(Continued)

FOREIGN PATENT DOCUMENTS

JP      9-220218     8/1997
JP   2003-144454     5/2003
(Continued)

OTHER PUBLICATIONS

Office Action dated Jun. 23, 2020 in corresponding Japanese Patent Application No. 2016-177981, 5 pages.

*Primary Examiner* — Xin Jia
(74) *Attorney, Agent, or Firm* — Oblon, McClelland, Maier & Neustadt, L.L.P.

(57) ABSTRACT

A medical image diagnostic apparatus according to an embodiment includes processing circuitry. The processing circuitry extracts a reference line of a region of interest included in a medical image collected from a subject. The processing circuitry sets feature points in the region of interest based on the reference line and a contour of the region of interest. The processing circuitry presents pieces of identification information for identifying the positions of the set feature points. The processing circuitry receives a contactless input for selecting a specific piece of identification information from the pieces of identification information presented in the medical image. Based on the specific piece of identification information for which the contactless input is received, the processing circuitry acquires the position of the feature point having the corresponding piece of identification information in the medical image.

18 Claims, 12 Drawing Sheets

(51) Int. Cl.
*G06F 3/0484* (2013.01)
*G06T 7/73* (2017.01)
*A61B 6/06* (2006.01)
*G06T 7/00* (2017.01)
*G06F 3/01* (2006.01)
*G06F 3/16* (2006.01)

(52) U.S. Cl.
CPC ........ *G06F 3/04845* (2013.01); *G06T 7/0014* (2013.01); *G06T 7/73* (2017.01); *A61B 6/4441* (2013.01); *A61B 6/481* (2013.01); *G06F 3/013* (2013.01); *G06F 3/04842* (2013.01); *G06F 3/16* (2013.01); *G06T 2200/04* (2013.01); *G06T 2207/10116* (2013.01); *G06T 2207/20101* (2013.01); *G06T 2207/30016* (2013.01); *G06T 2207/30101* (2013.01)

(58) Field of Classification Search
CPC .. G06F 3/013; G06F 3/04842; G06F 3/04845; G06F 3/16; G06T 2200/04; G06T 2207/10116; G06T 2207/20101; G06T 2207/30016; G06T 2207/30101; G06T 7/0014; G06T 7/73
See application file for complete search history.

(56) References Cited

U.S. PATENT DOCUMENTS

| | | |
|---|---|---|
| 2011/0190634 A1 | 8/2011 | Kawagishi et al. |
| 2012/0099776 A1* | 4/2012 | Maeda .................. A61B 5/055 382/131 |
| 2015/0141814 A1* | 5/2015 | Lee ...................... A61B 6/5217 600/425 |
| 2016/0125262 A1* | 5/2016 | Ishihara ................ G06F 16/583 382/131 |

FOREIGN PATENT DOCUMENTS

| | | |
|---|---|---|
| JP | 2008-43524 | 2/2008 |
| JP | 2008-99929 A | 5/2008 |
| JP | 2011-115280 A | 6/2011 |
| JP | 2011-177495 | 9/2011 |

* cited by examiner

US 10,849,583 B2

MEDICAL IMAGE DIAGNOSTIC APPARATUS AND MEDICAL IMAGE PROCESSING APPARATUS

CROSS-REFERENCE TO RELATED APPLICATIONS

This application is based upon and claims the benefit of priority from Japanese Patent Application No. 2016-177981, filed on Sep. 12, 2016; the entire contents of which are incorporated herein by reference.

FIELD

Embodiments described herein relate generally to a medical image diagnostic apparatus and a medical image processing apparatus.

BACKGROUND

A measurement process, an analyzing process, and the like of a lesion area have been conventionally executed using a medical image collected by a medical image diagnostic apparatus. For example, before a physician carries out coiling for filling an aneurysm with a coil, or stenting placing a stent in a stenosis, using an X-ray angiography apparatus, the physician measures the volume of the aneurysm or the size of the blood vessel with a stenosis, for example, using a three-dimensional X-ray image collected in advance. The physician then selects the coil or the stent that is to be used in the procedure, by making such measurements.

Before the measurement process, the analysis process, the like mentioned above is executed, an operator makes a designating operation on the medical image. For example, to carry out an operation such as coiling or stenting, the operator (such as a physician responsible for the procedure) makes a designating operation for designating the aneurysm or the stenosis on the three-dimensional X-ray image, by operating an input device such as a mouse.

DETAILED DESCRIPTION

According to an embodiment, a medical image diagnostic apparatus includes processing circuitry. The processing circuitry is configured to extract a reference line of a region of interest included in a medical image collected from a subject. The processing circuitry is configured to set feature points in the region of interest based on the reference line and a contour of the region of interest. The processing circuitry is configured to present pieces identification information for identifying positions of the set feature points. The processing circuitry is configured to receive a contactless input for selecting a specific piece of identification information from the pieces of identification information presented in the medical image. The processing circuitry is configured to acquire, based on the specific Niece of identification information for which the contactless input is received, a position of the feature point having the corresponding piece of identification information in the medical image.

A medical image diagnostic apparatus and a medical image processing apparatus according to some embodiments will now be explained in detail, with reference to the accompanying drawings. In the explanation below, an X-ray angiography apparatus will be used as an example of the medical image diagnostic apparatus according to the embodiments.

First Embodiment

Figure 1A:
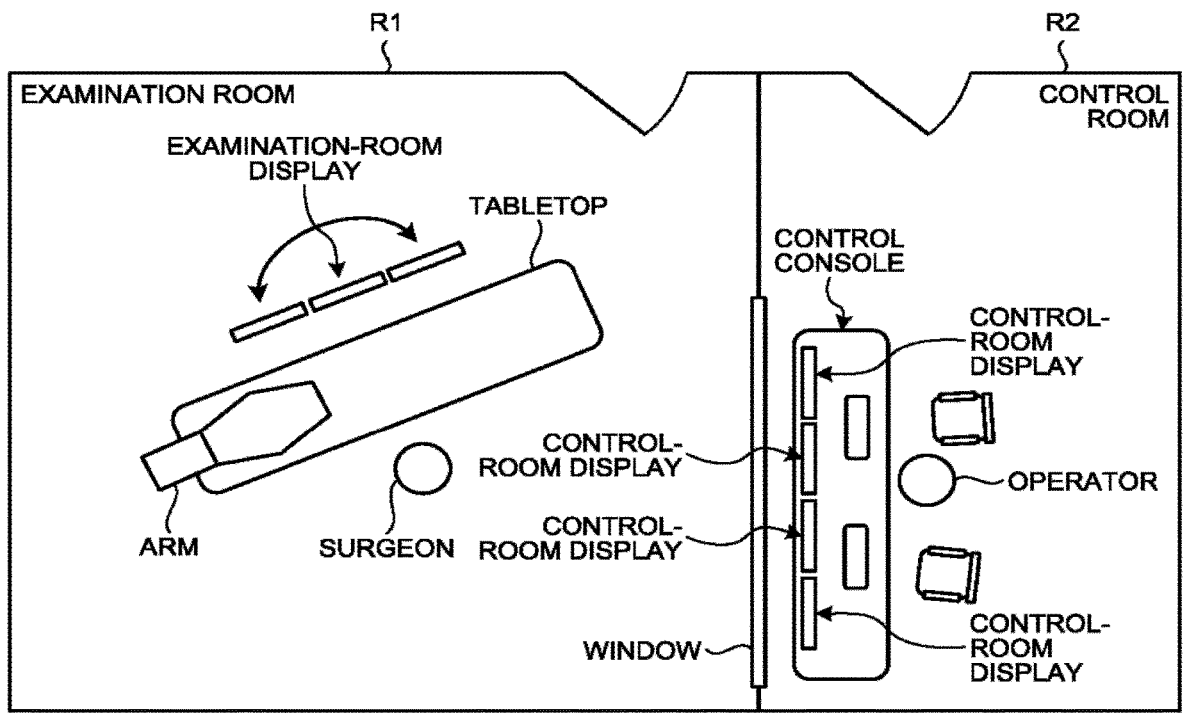
FIG. 1A is a schematic for explaining an example of an X-ray angiography apparatus according to a first embodiment.
Figure 1B:
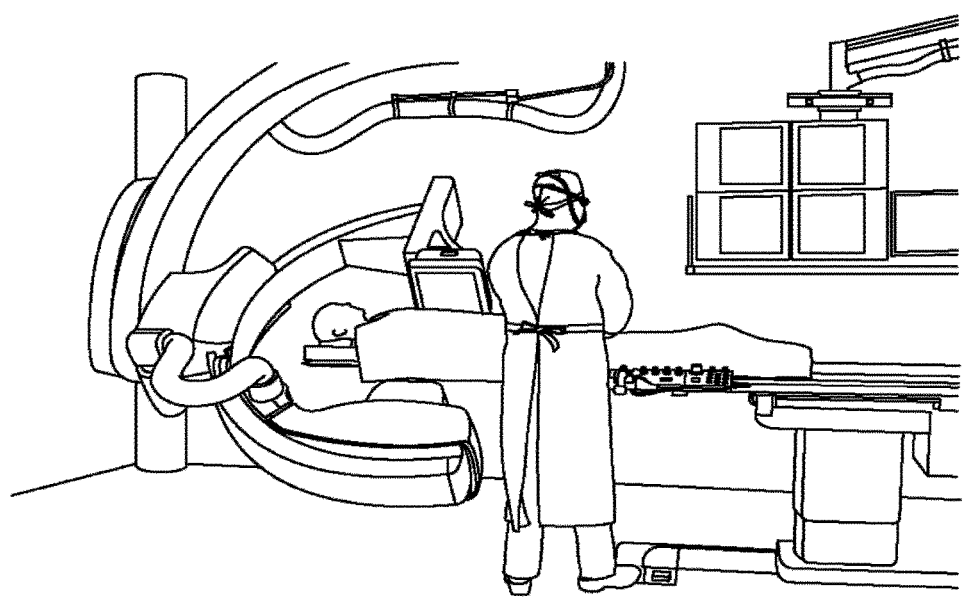
FIG. 1B is a schematic for explaining the example of the X-ray angiography apparatus according to the first embodiment.

To begin with, an example of an X-ray angiography apparatus according to a first embodiment will now be explained with reference to FIGS. 1A and 1B. FIGS. 1A and 1B are schematics for explaining an example of an X-ray angiography apparatus according to the first embodiment. The X-ray angiography apparatus includes a main apparatus having an arm and a tabletop that are installed in an examination room R1 in which a diagnosis or a treatment of the brain or the circulatory system such as the heart, is conducted, as illustrated in FIG. 1A. A control console for performing operations for controlling the main apparatus is installed in the control room R2, as illustrated in FIG. 1A.

A plurality of examination room displays and a plurality of control room displays, for example, are installed in the examination room R1 and the control room R2, respectively. The examination room displays are observed by a surgeon (physician) or nurses performing a procedure, for example. The control room displays are observed by an operator making operations for controlling the main apparatus. To explain the operation using an example, in the examination room R1, the physician performing a procedure carries out a cerebrovascular treatment, for example, by observing fluoroscopic image displayed on the examination room displays. In the control room R2, for example, a technologist, for example, adjusts parameters or the like, by operating the control console based on instructions of the surgeon while observing the control room displays.

The X-ray angiography apparatus according to the first embodiment enables a designating operation to be performed easily. As mentioned earlier, an operator (a physician responsible for the procedure) makes various designating operations on an X-ray image, for example, using the X-ray angiography apparatus, when coiling or stenting is carried out. To measure the volume of an aneurysm, or the size of the blood vessel with a stenosis, for example, the physician makes a designating operation for designating the position of the aneurysm or the stenosis in the X-ray image.

The X-ray angiography apparatus according to the first embodiment enables the designating operation to be performed easily under such circumstances. Specifically, the X-ray angiography apparatus enables the designating operation to be performed easily by allowing an operator to make a designating operation via a contactless input. The contactless input according to the embodiment is an input executed without making an operation of an input device, such as a mouse, a keyboard, or a switch, and examples of the contactless input include a voice input and an eye-gaze input. In other words, the X-ray angiography apparatus according to the embodiment receives a designating operation of the operator designating an intended position using voice or eye gaze.

For example, as illustrated in FIG. 1B, a physician who is carrying out the procedure using the X-ray angiography apparatus makes a designating operation for designating a position of an aneurysm, a stenosis, or the like using voice or eye gaze, while observing the X-ray images of a subject displayed in the examination room displays installed in the examination room R1. The X-ray angiography apparatus receives the designating operation made by the physician via a contactless input, and measures the volume of the aneurysm or the size of the blood vessel. In this manner, compared with an X-ray angiography apparatus with a contact-based input, which uses a mouse or a switch, the X-ray angiography apparatus can omit burdens of the operator putting on a pair of gloves for preventing the contamination of the surgical sterile gloves, or of going to the control room R2 from the examination room R1, for example, so the operator can make the designating operation easily.

Figure 2:
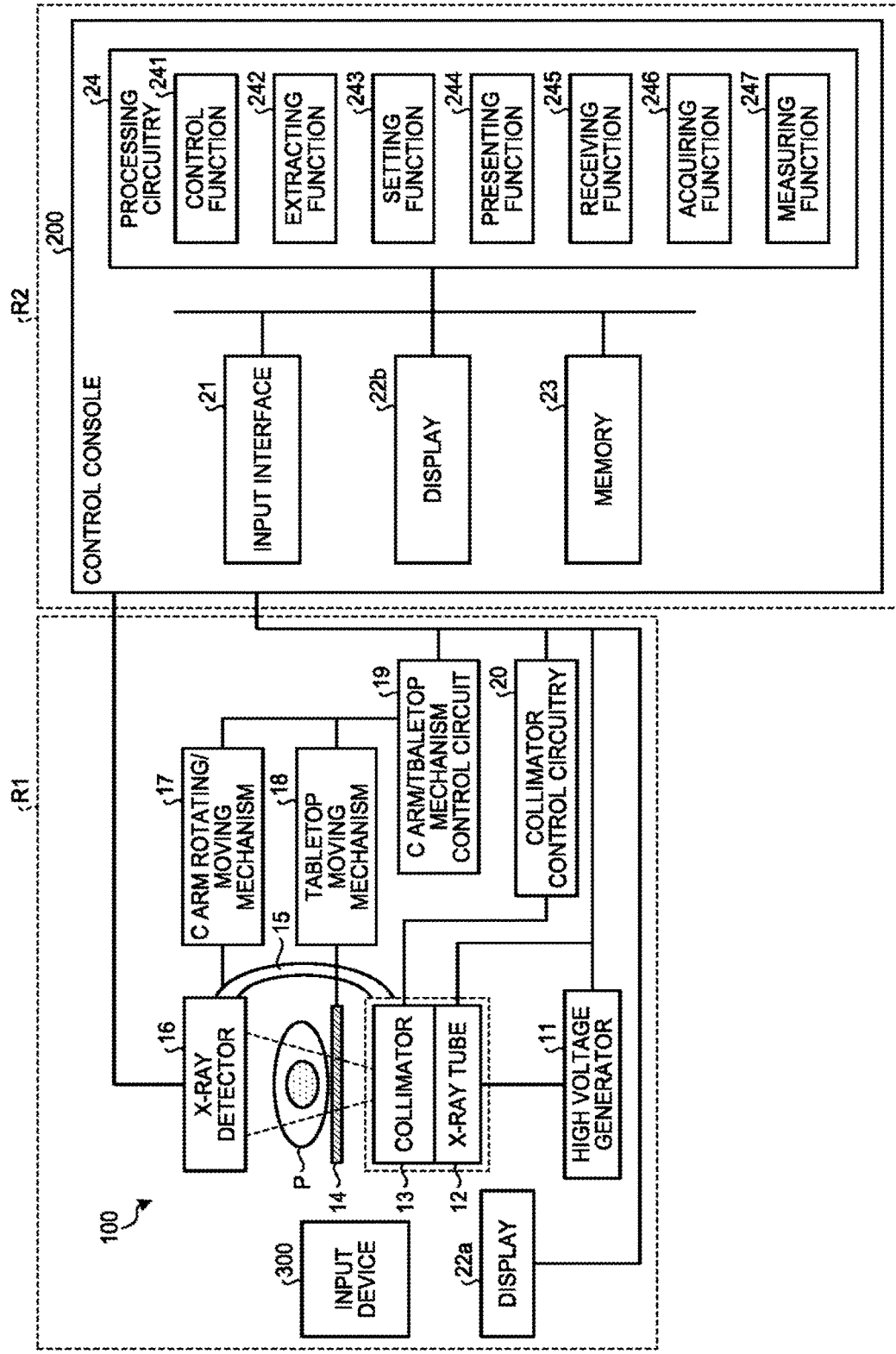
FIG. 2 is a schematic illustrating an example of a configuration of the X-ray angiography apparatus according to the first embodiment.

A designating operation via the contactless input described above will now be explained in detail. FIG. 2 is a schematic illustrating an example of a configuration of the X-ray angiography apparatus 1 according to the first embodiment. As illustrated in FIG. 2, the X-ray angiography apparatus 1 according to the first embodiment includes a main apparatus 100 and a control console 200. The main apparatus 100 includes, as illustrated in FIG. 2, a high voltage generator 11, an X-ray tube 12, a collimator 13, a tabletop 14, a C arm 15, an X-ray detector 16, a C arm rotating/moving mechanism 17, a tabletop moving mechanism 18, C arm/tabletop mechanism control circuitry 19, collimator control circuitry 20, and a display 22a, and the main apparatus 106 is installed in the examination room R1. The control console 200 includes, as illustrated in FIG. 2, an input interface 21, a display 22b, a memory 23, and processing circuitry 24, and is installed in the control room R2. The control console 200 then communicates with an input device 300 installed in the examination room R1. Although not illustrated in FIG. 2, the X-ray angiography apparatus 1 also includes an injector for injecting contrast agent into a subject. P, via a catheter inserted in the subject P.

The input device 300 receives an input operation from the operator via a contactless input. The input device 300 is, for example, a voice recognition apparatus, and recognizes the voice information uttered by the operator (physician), and transmits the recognized voice information to the control console 200. To explain the operation with an example, the input device 300 recognizes voice information for designating position information in an X-ray image displayed on the display 22a, and transmits the recognized position information to the control console 200.

As another example, the input device 300 may be a line-of-sight recognition apparatus and recognizes the line of sight of the physician, recognizing the viewpoint of the physician who is observing the image displayed on the display 22a. Specifically, the input device 300 recognizes where the viewpoint of the observer is in the image displayed on the display 22a. For example, the input device 300 is a device having a camera for capturing an image of the physician, and converts the point at which the line of sight intersects with the plane extending along the display surface of the display 22a, into point coordinates in a two-dimensional coordinate system plotted onto the display surface, and transmits the point coordinates to the control console 200.

To explain the operation with an example, the input device 300 detects the positions of the eyes and the line of sight (eye gaze) of the physician based on the information acquired from the camera and detects the viewpoint (gaze point) of physician on the display 22a. A two-dimensional (X axis, Y axis) coordinate system, for example, is plotted to the display surface of the display 22a in advance. The input device 300 detects a line of sight of the physician based on the information acquired from the camera, and calculates the point at which the detected line of sight intersects with the display surface of the display 22a. The input device 300 calculates the coordinates of the intersection point in the coordinate system having the X and Y axes, by referring to the two-dimensional coordinate information of the display surface of the display 22a, and transmits the coordinates to the control console 20C. Any method having been conventionally used may be used as the method for detecting the line of sight, an example of which includes limbus tracking (sclera reflection method) in which the difference in the reflectance to light between the sclera (white of the eye) and the cornea (iris) is used to measure the eye movement. The input device 300 may be a device installed near the monitor, for example, or may be a wearable terminal device such as a pair of glasses.

The high voltage generator 11 generates a high voltage and supplies the generated high voltage to the X-ray tube 12, under the control of the processing circuitry 24. The X-ray tube 12 generates X-rays using the high voltage supplied by the high voltage generator 11.

The collimator 13 is narrowed down to irradiate the region of interest in the subject P with the X-rays generated by the X-ray tube 12, under the control of the collimator control circuitry 20. As an example, the collimator 13 has four slidable collimator vanes. The collimator 13 is narrowed down to irradiate the subject P with the X-rays generated by the X-ray tube 12 by causing the collimator vanes to slide under the control of the collimator control circuitry 20. The X-ray tube 12 and the collimator 13 are sometimes collectively referred to as an X-ray tube device. The tabletop 14 is a bed on which the subject P is laid, and is placed on a table not illustrated. The subject P is not included in the main apparatus 100.

The X-ray detector 16 detects the X-rays having passed through the subject P. For example, the X-ray detector 16 includes detector elements that are arranged in a matrix shape. Each of the detector elements converts the X-rays having passed through the subject P into electrical signals, accumulates the electrical signals, arid transmits the accumulated electrical signals to the processing circuitry 24.

The C arm 15 holds the X-ray tube 12, the collimator 13, and the X-ray detector 16. The C arm 15 positions the X-ray tube 12 and the collimator 13 in a manner facing the X-ray detector 16, with the subject P interposed therebetween. The C arm 15 is rotated at a high speed, like a propeller, around the subject P laying on the tabletop 14 by a motor provided to a support (not illustrated). The C arm 15 is supported rotatably about the three axes, the X, the Y, and Z axes intersecting with one another perpendicularly, and is caused to rotate about each of the axes individually, by a driving unit not illustrated. Illustrated in FIG. 1 is an example of a single-plane X-ray angiography apparatus 1 having one C arm 15, but the X-ray angiography apparatus according to the embodiment may also be a biplane X-ray angiography apparatus having two pairs of arms. In such a configuration, each of the arms supports the X-ray tube 12, the collimator 13, and the X-ray detector 16.

The C arm rotating moving mechanism 17 is a mechanism for rotating and moving the C arm 15, and the tabletop moving mechanism 18 is a mechanism for moving the tabletop 14. The C arm/tabletop mechanism control circuitry 19 adjusts the rotation and the movement of the C arm 15, and the movement of the tabletop 14, by controlling the C arm rotating/moving mechanism 17 and the tabletop moving mechanism 18, under the control of the processing circuitry 24. The collimator control circuitry 20 controls the range of the subject P irradiated with X-rays by adjusting the amount by which the collimator vanes provided to the collimator 13 are opened, under the control of the processing circuitry 24.

The input interface 21 is implemented with a trackball, a switch button, a mouse, or a keyboard, for performing various settings. The input interface 21 is connected to the processing circuitry 24, and converts an input operation received from an operator such as a technologist into an electrical signal in the control room R2 and outputs he electrical signal to the processing circuitry 24.

The display 22a and the display 22b display a graphical user interface (GUI) for receiving an instruction of the operator, or image data stored in the memory 23, for example. The display 22a is an examination room display, and the display 22b is a control room display, for example. Each of the display 22a and the display 22b may have a plurality of displays. For example, the display 22a and the display 22b display a real-time fluoroscopic image, a three-dimensional image, or a three-dimensional roadmap (3DRM). The 3DRM is an image in which a real-time fluoroscopic image is superimposed over a projection image generated from the volume data collected by the main apparatus 100. The display 22a displays various types of information generated by the processing circuitry 24, which will be described later. Specifically, the display 22a displays information indicating position information on the X-ray image.

The memory 23 stores therein projection data and an X-ray image generated by the processing circuitry 24, or reconstructed volume data and a three-dimensional image, for example. The memory 23 also stores therein computer programs corresponding to various functions read and executed by the circuits illustrated in FIG. 2. To explain the operation with an example, the memory 23 stores therein a computer program corresponding to a control function 241, a computer program corresponding to an extracting function 242, a computer program corresponding to a presenting function 244, a computer program corresponding to a receiving function 245, a computer program corresponding to an acquiring function 246, and a computer program corresponding to a measuring function 247, all of which are read and executed by the processing circuitry 24.

The processing circuitry 24 controls operations of the entire X-ray angiography apparatus 1 by reading a computer program corresponding to the control function 241 from the memory 23, and executing the computer program. For example, the control function 241 controls ON/OFF of or the dose of the X-rays with which the subject P is irradiated, by adjusting the voltage to be supplied to the X-ray tube 12 by controlling the high voltage generator 11, based on an instruction of the operator transferred from the input interface 21. As another example, the control function 241 adjusts the rotation and the movement of the C arm 15 and the movement of the tabletop 14, based on the instruction of the operator, by controlling the C arm/tabletop mechanism control circuitry 19. To explain the operation with another example, the control function 241 controls rotography for collecting projection data at a predetermined frame rate while rotating the C arm 15. While controlling the rotation of the C arm 15, the control function 241 controls to cause the X-ray tube 12 to output X-rays continuously or intermittently by controlling the high voltage generator 11, and to cause the X-ray detector 16 to detect the X-rays having passed through the subject P. As another example, the control function 241 controls the range of the subject P irradiated with the X-rays by adjusting the degree by which the collimator vanes of the collimator 13 are opened, by controlling the collimator control circuitry 20 based on an instruction of the operator.

The control function 241 also controls generation and display of X-ray images based on an instruction of the operator. Specifically, the control function 241 generates image data (projection data) using electrical signals that are resultant of causing the X-ray detector 16 to convert the X-rays, and stores the generated projection data in the memory 23. For example, the control function 241 generates projection data by performing a current-to-voltage conversion, an analog-to-digital (A/D) conversion, and a parallel-to-serial conversion to the electrical signals received from the X-ray detector 16, and stores the generated projection data in the memory 23. The control function 241 also generates an X-ray image from the generated projection data, and stores the generated X-ray image in the memory 23.

The control function 241 is also capable of reconstructing reconstruction data (volume data) from the projection data collected via the rotography executed by the main apparatus 100. For example, the control function 241 reconstructs volume data from the projection data stored in the memory 23 and stores the reconstructed volume data in the memory 23. The control function 241 also generates a three-dimensional X-ray image (three-dimensional image) from the volume data and stores the three-dimensional X-ray image in the memory 23. For example, the control function 241 generates a volume rendering image or a multi-planar reconstruction (MPR) image from the volume data. The control function 241 then stores the generated three-dimensional image in the memory 23.

The control function 241 controls to display a GUI for receiving instructions of the operator or an X-ray image stored in the memory 23 on the display 22a and the display 22b. The control function 241 is also capable of controlling to cause the injector to inject contrast agent by transmitting a contrast agent injection start signal and a contrast agent injection end signal.

In addition to the control function 241 described above, the processing circuitry 24 according to the first embodiment receives a designating operation via a contactless input, and executes a process corresponding to the received designating operation, by executing the extracting function 242, a setting function 243, the presenting function 244, the receiving function 245, the acquiring function 246, and the measuring function 247 illustrated in FIG. 2. The processing circuitry is an example of the processing circuitry as described in the appended claims.

In the X-ray angiography apparatus 1 illustrated in FIG. 2, the processing functions are stored in the memory 23 as computer-executable programs. Each of the C arm/tabletop mechanism control circuitry 19, the collimator control circuitry 20, and the processing circuitry 24 is a processor implementing the function of the corresponding computer program by reading and executing the computer program from the memory 23. In other words, each of these circuits having read the corresponding computer program comes to have a function corresponding to the read computer program.

Explained above is a configuration of the X-ray angiography apparatus 1 according to the first embodiment. The process executed by the processing circuitry 24 will now be explained in detail. Used in the explanation hereunder is an example in which a designating operation for designating a position in the brain artery is performed via a contactless input. To designate a position, to begin with, the control function 241 collects a three-dimensional image of the brain artery to which the designating operation via a contactless input is to be performed.

For example, the control function 241 controls the high voltage generator 11 and the C arm/tabletop mechanism circuitry 19 to output X-ray pulses, while rotating the C arm 15 by approximately 200 degrees around the subject, to collect projection data from each direction across the approximately 200 degrees around the subject, and to reconstruct volume data by performing a reconstruction process using the collected projection data. The control function 241 controls injection of the contrast agent via the injector not illustrated, for example, and collects a mask image and a contrast image. In other words, the control function 241 collects projection data for a mask image from each direction across the approximately 200 degrees around the subject by outputting X-ray pulses while rotating the C arm 15 by approximately 200 degrees around the subject not having received an injection of the contrast agent. The control function 241 then controls the injector to inject the contrast agent into the subject, and collects projection data for a contrast image from each direction across the approximately 200 degrees around the subject by outputting X-ray pulses while rotating the C arm 15 by approximately 200 degrees around the subject.

Figure 3:
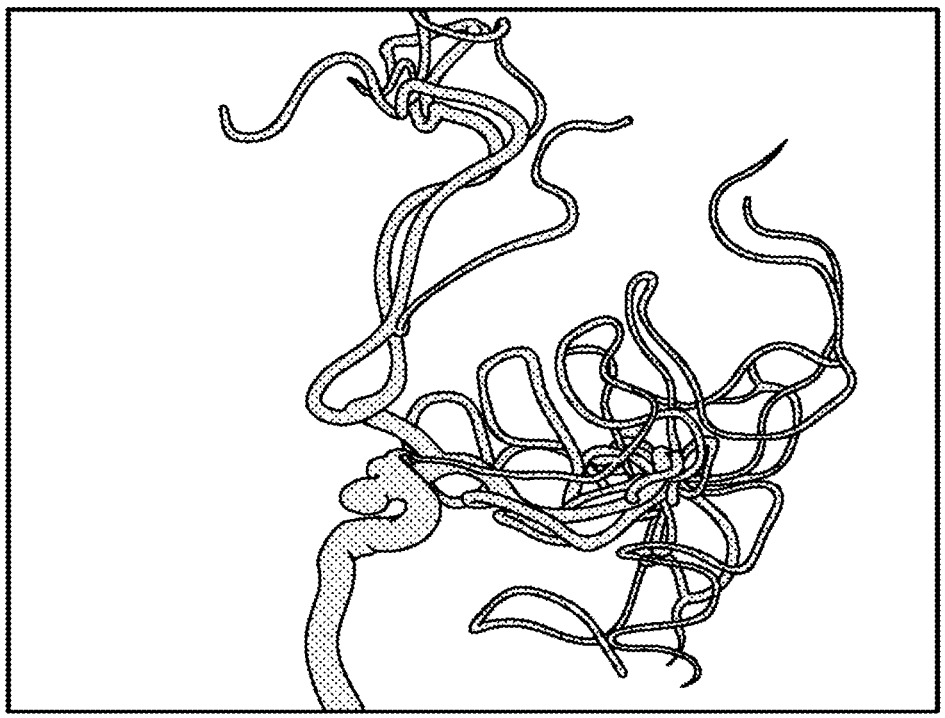
FIG. 3 is a schematic illustrating an example of a three-dimensional image generated by a control function according to the first embodiment.

The control function 241 then takes a difference between the projection data of the mask image and the projection data of the contrast image, and reconstructs the volume data from the projection data with the difference taken. The control function 241 generates a three-dimensional contrast image of the brain artery by executing a volume rendering process to the reconstructed volume data, for example. FIG. 3 is a schematic illustrating an example of a three-dimensional image generated by the control function 241 according to the first embodiment. The control function 241 generates a three-dimensional contrast image of the brain artery illustrated in FIG. 3 by executing the control described above, for example. The three-dimensional contrast image of the brain artery illustrated in FIG. 3 may be displayed on the display 22a.

Referring back to FIG. 2, the extracting function 242 extracts a reference line of a region of interest from the medical image collected from the subject. Specifically, the extracting function 242 extracts a core line of the region of interest in the volume data. For example, using the volume data used in generating the contrast image of the brain artery illustrated in FIG. 3, the extracting function 242 extracts the core line of the brain artery imaged with the contrast agent. To explain the operation with an example, the extracting function 242 extracts the core line of the brain artery using a method such as vessel tracking or line-thinning of the internal region.

The setting function 243 then sets feature points to the region of interest, based on the core line and the contour of the region of interest. Specifically, the setting function 243 sets feature points based on positions plotted along the direction of the core line of the region of interest, and positions plotted along a direction perpendicular to the direction of the core line of the region of interest. The feature points set by the setting function 243 will be described later in detail.

The presenting function 244 presents pieces of identification information for identifying the positions of the set feature points. Specifically, the presenting function 244 presents pieces of identification information for identifying positions in the region of interest based on the core line in the medical image. Assuming that the designating operation is performed to an aneurysm in the brain artery, the presenting function 244 according to the first embodiment presents identification information for identifying the region of interest of which detailed identification information is to be presented. For example, the presenting function 244 presents terminal point identification information for identifying a terminal point of the core line to the corresponding position in the region of interest. In other words, when the brain artery has an aneurysm, the core line extraction stops at the position of the aneurysm (a terminal point of the core line will exist at the position of the aneurysm). Therefore, the presenting function 244 presents a label for designating the position of the brain aneurysm at the position of the terminal point of the core line in the contrast image.

Figure 4:
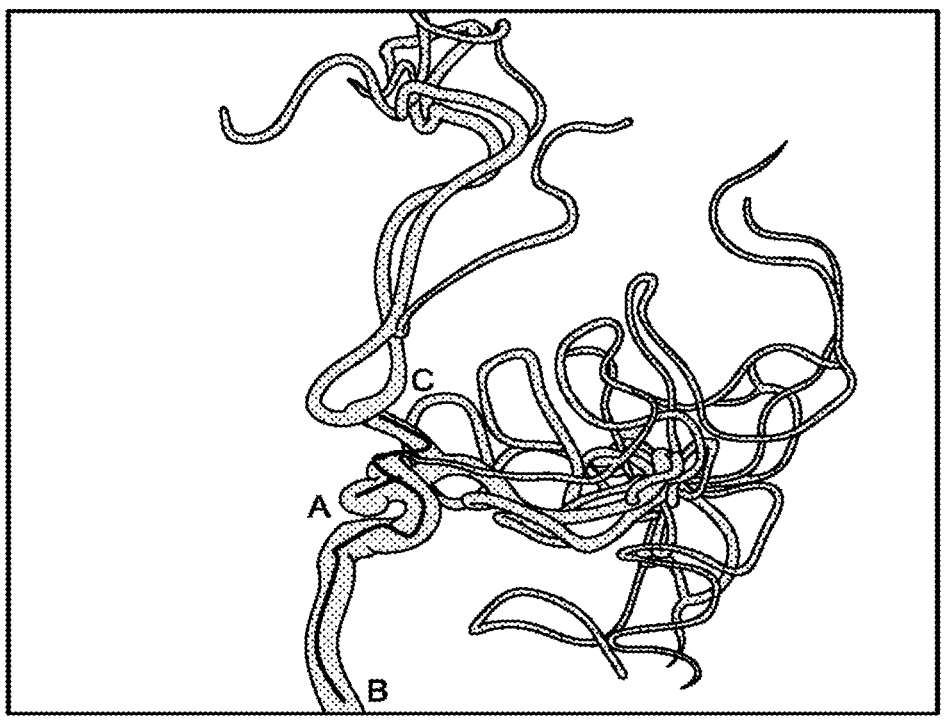
FIG. 4 is a schematic illustrating an example of labels visually presented by a presenting function according to the first embodiment.

FIG. 4 is a schematic illustrating an example of the labels visually presented by the presenting function 244 according to the first embodiment. For example, the presenting function 244 visually presents the core lines, and terminal point labels A, B, and C indicating the terminal points of the core lines, on the three-dimensional contrast image of the brain artery on the display 22*a*, as illustrated in FIG. 4. When the region of the interest is a brain aneurysm, the presenting function 244 can visually present a terminal point label on a blood vessel that is likely to develop a brain aneurysm. For example, the presenting function 244 presents a terminal point label to a al point in the region in which the diameter of a brain artery is equal to or larger than a predetermined threshold.

In other words, the presenting function 244 extracts a region corresponding to a brain artery based on the luminance values of the voxels in the volume data, and calculates the diameter of the brain artery at each position illustrated in FIG. 4, using the extracted region. By comparing the calculated diameter with a predetermined threshold, the presenting function 244 extracts the core line of a brain artery region having a diameter equal to or larger than the predetermined threshold, and the terminal point of the core line of the brain artery region. The presenting function 244 then visually presents the terminal point labels A, B, and C for identifying the extracted terminal points on the contrast image. In this manner, the operator can designate the position of the brain aneurysm using the terminal point labels. The predetermined threshold related to the diameter can be set in any value.

The presenting function 244 may also present a terminal point label for a terminal point the distance of which to a branch is equal to or shorter than a predetermined threshold, among the terminal points of the core lines of the region of interest. For example, a terminal point of the core line of the brain aneurysm is at a short distance from a branch of the core line of the brain artery. To achieve this goal, the presenting function 244 calculates the distance from a terminal point of the core line to the branch and compares the calculated distance with the predetermined threshold. The presenting function 244 then visually presents the terminal point label only for the terminal point that is distant from the branch by a distance equal to or shorter than the predetermined threshold, on the display 22*a*. To explain the operation with an example, the presenting function 244 calculates a distance from each of the terminal points corresponding to the terminal point labels A, B, and C, illustrated in FIG. 4, to a branch. For example, the presenting function 244 calculates a distance from the terminal point of the core line corresponding to the terminal point label A to the branch (the position intersecting with the core line connecting the terminal point labels B and C). If the calculated distance is equal to or shorter than a predetermined threshold, the presenting function 244 visually presents the terminal point label A on the contrast image. In the same manner for each of the terminal point labels B and C, the presenting function 244 determines whether the terminal point labels B and C are to be visually presented on the contrast image, by calculating a distance from the corresponding terminal point to the branch and comparing the calculated distance with the predetermined threshold. The predetermined threshold related to the distance from the terminal point to the branch may be set to any value.

The presenting function 244 also presents pieces of identification information for identifying positions in the region of interest. For example, the presenting function 244 displays labels indicating the positions in the brain aneurysm. The labels displayed by the presenting function 244 will be described later in detail.

Referring back to FIG. 2, the receiving function 24.5 receives a contactless input for selecting a specific piece of identification information, from a plurality of pieces of identification information presented on the medical image. Specifically, the receiving function 245 receives voice information, for example, from the input device 300, and sends the received voice information or the like to the acquiring function 246. For example, when selected is identification information related to a brain aneurysm, the receiving function 245 receives a contactless input for selecting a terminal point label for designating the brain aneurysm, and a contactless input for selecting a label for designating a specific position in the brain aneurysm.

When received is a contactless input for selecting a terminal point label, the receiving function 245 receives a contactless input for selecting a specific terminal point label from a plurality of terminal point labels presented in the region of interest. For example, the presenting function 244 displays a contrast image of the brain artery having the terminal point labels A, B, and C illustrated in FIG. 4 on the display 22*a* in the examination room R1. The physician carrying out the procedure in the examination room R1 observes the contrast image of the brain artery displayed on the display 22*a*, checks the position of the brain aneurysm, and selects the "terminal point label A", which is a terminal point of the core line of the brain aneurysm, using his/her voice. The physician selects the "terminal point label A" by saying "terminal point label A", for example.

Figure 5:
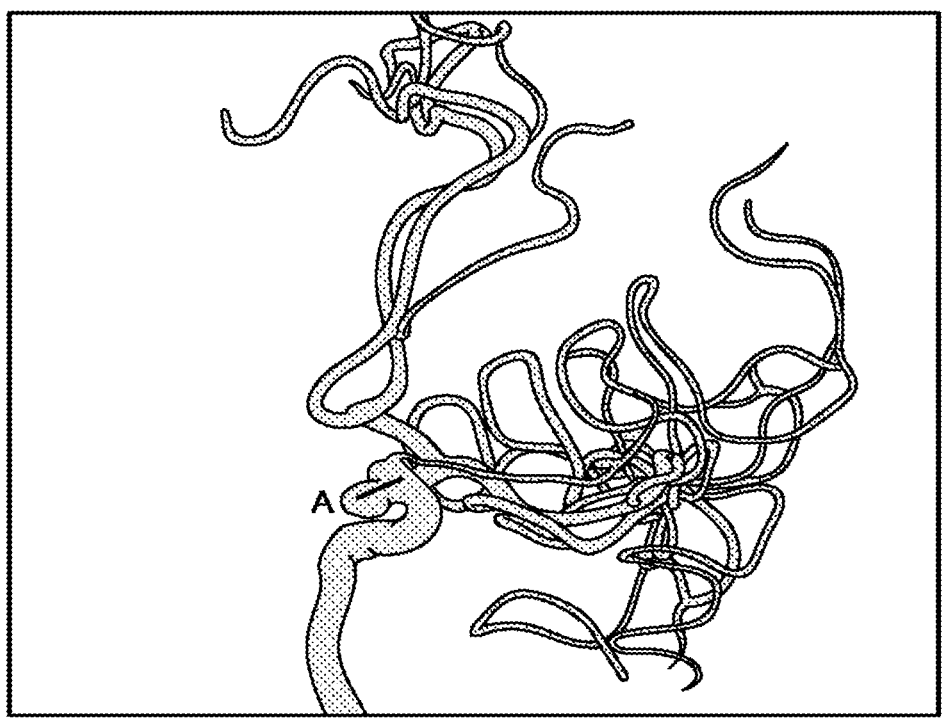
FIG. 5 is a schematic illustrating an example of a presenting process performed by the presenting function according to the first embodiment.

The input device 300 transmits the "terminal point label A" uttered by the physician to the processing circuitry 24. The receiving function 245 in the processing circuitry 24 sends the "terminal point Zabel A" received from the input device 300 to the acquiring function 246. In this manner, for example, the position of the brain aneurysm illustrated in FIG. 5 is selected, and only the terminal point label A corresponding to the brain aneurysm, and the core line corresponding to the terminal point label A are selected. Once the receiving function 245 receives a selection of a terminal point label, as illustrated in FIG. 5, the presenting function 244 displays the contrast image including only the selected terminal point label A and core line on the display 22*a*. FIG. 5 is a schematic illustrating an example of a presenting process performed by the presenting function 244 according to the first embodiment. The receiving function 245 then receives a contactless input for selecting a label for designating a specific position in the brain aneurysm, but this process will be described later in detail.

The acquiring function 246 acquires the position of the feature point having the corresponding identification information in the medical image, based on the specific piece of identification information for which a contactless input is received. Specifically, the acquiring function 246 acquires the position information of the position defined by the specific piece of identification information for which a contactless input is received. More specifically, the acquiring function 246 acquires the position information of the position corresponding to the identification information received by the receiving function 245 via the input device 300. For example, when the region of interest is a brain aneurysm, the acquiring function 246 acquires the position information corresponding to a terminal point label received by the receiving function 245, and the position information corresponding to a label designating a specific position in the brain aneurysm.

When acquired is the position information corresponding to the terminal point label received by the receiving function 245, the acquiring function 246 acquires the coordinate information of the voxel representing a region of the core line ;brain aneurysm) corresponding to the terminal point label selected via a contactless input such as voice. In other words, the acquiring function 246 acquires the coordinate information of the brain aneurysm in the volume data of the contrast image on which the terminal point label is selected. For example, based on the coordinate information of the terminal point label A in the volume data, the acquiring function 246 acquires the coordinate information of the region corresponding for the core line with the terminal point label A, from the volume data.

As mentioned earlier, when the region of interest is a brain aneurysm, the setting function 243, the presenting function 244, the receiving function 245, and the acquiring function 246 in the processing circuitry 24 acquire the position of the brain aneurysm in the three-dimensional contrast image via a contactless input, such as an input of voice information. When the region of interest is a brain aneurysm, the setting function 243, the presenting function 244, the receiving function 245, and the acquiring function 246 included in the processing circuitry 24 also present the labels related to the positions in the brain aneurysm, receives an operation designating a label, and acquires the position information corresponding to the received label. These processes will now be explained in detail.

In this example, to begin with, the setting function 243 sets feature points based on the positions plotted along the direction of the core line of the region of interest, and the positions plotted along the direction perpendicular to the direction of the core line of the region of interest. Specifically, the setting function 243 sets feature points based on first planes that are plotted perpendicularly to the core line of the region of interest, and second planes that are plotted perpendicularly to the first planes and pass the core line. The presenting function 244 presents pieces of identification information for identifying the positions of the feature points. Specifically, the presenting function 244 presents pieces of first identification information (first labels) for identifying the positions plotted along the direction of the core line of the region of interest, and pieces of second identification information (second labels) for identifying the positions plotted along the direction perpendicular to the direction of the core line of the region of interest, at corresponding positions in the region of interest. More specifically, the presenting function 244 presents some labels for identifying the first planes that are plotted perpendicularly to the core line, as the first labels, and presents some labels for identifying the second planes that are plotted perpendicularly to the first planes and pass the core line, as the second labels. The presenting function 244 presents the first labels and the second labels for the core line having a terminal point with a terminal point label having been selected, in the region of interest.

Figure 6A:
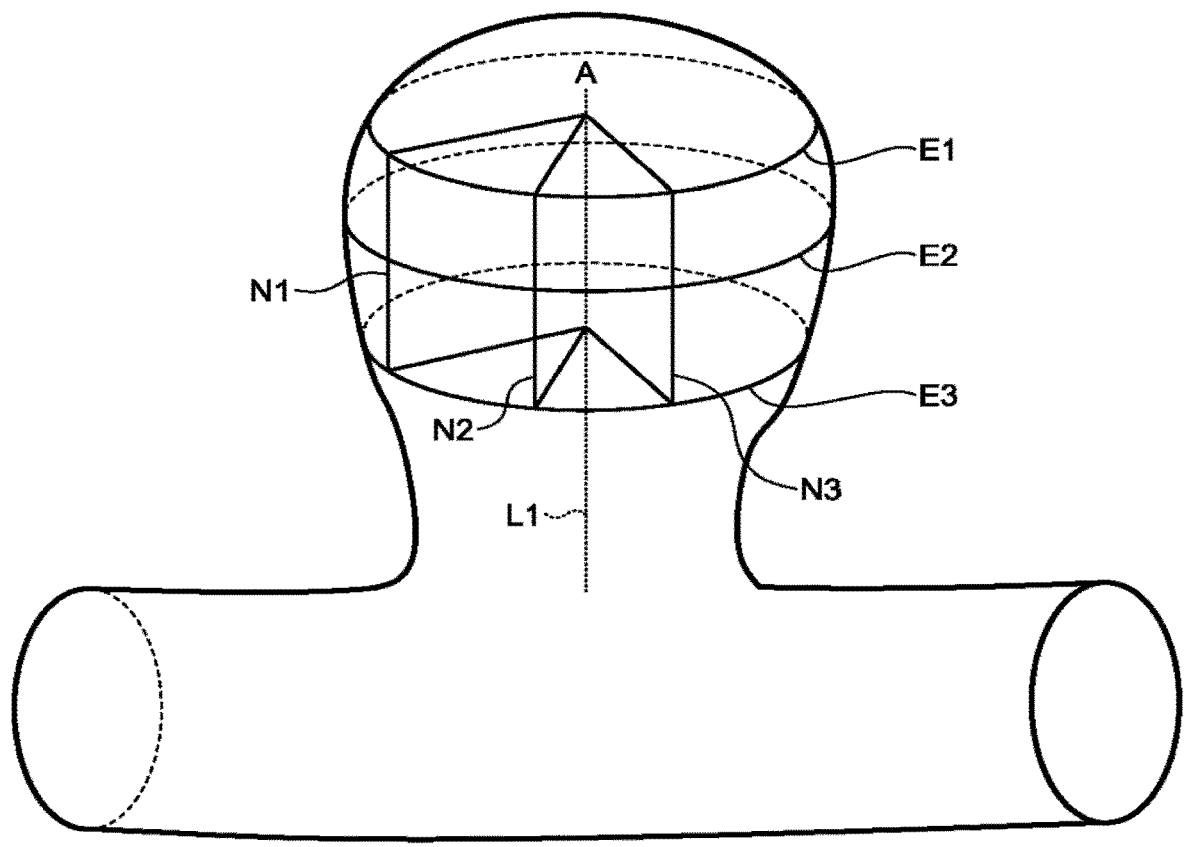
FIG. 6A is a schematic for explaining the labels set by a setting function according to the first embodiment.
Figure 6B:
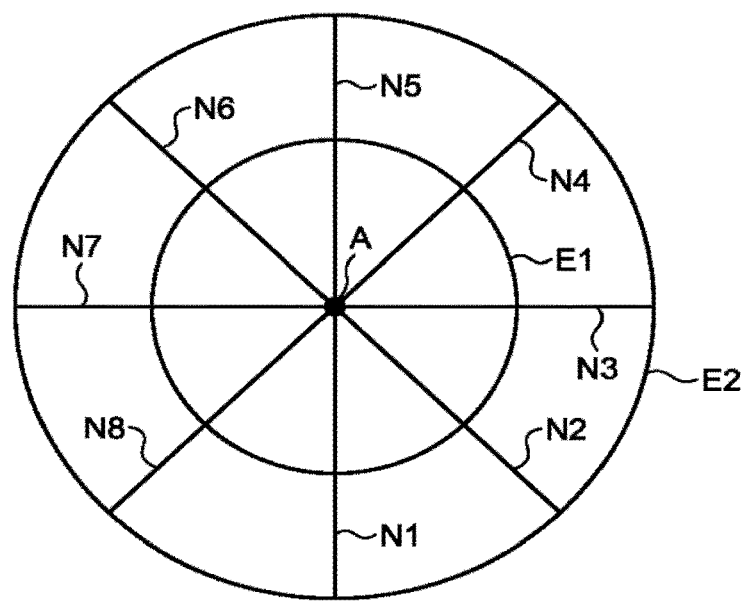
FIG. 6B is a schematic for explaining the labels set by the setting function according to the first embodiment.

FIGS. 6A and 6B are schematics for explaining the labels set by the setting function 243 according to the first embodiment. Illustrated in FIG. 6A is an example in which the labels are set to a brain aneurysm corresponding to a core line having the terminal point label A. FIG. 6B illustrates a positional relation of the labels when FIG. 6A is seen in the direction along a core line L1. For example, the setting function 243 sets feature points by setting the first labels and the second labels illustrated in FIGS. 6A and 6B to the core line having the terminal point label A, a designation operation of which is received by the receiving function 245. In other words, the setting function 243 sets planes E1, E2, and E3 (first labels) intersecting perpendicularly to the core line L1 having the terminal point label A, as illustrated in FIG. 6A. The setting function 243 also sets planes N1, N2, and N3 (second labels) intersecting perpendicularly to at least one of the planes E1, E2, E3, and passing the core line L1.

The setting function 243 sets the second labels at equal intervals across 360 degrees around the core line L1, as illustrated in FIG. 6B. In other words, the setting function 243 sets the planes of N1, N2, N3, N4, N5, N6, N7, and N8 at positions at equal intervals about the core line L1, as illustrated in FIG. 6B, as the second labels. By setting the first labels and the second labels in a manner described above, the setting function 243 sets the feature points (the points at which the first labels intersect with the second labels).

Figure 7:
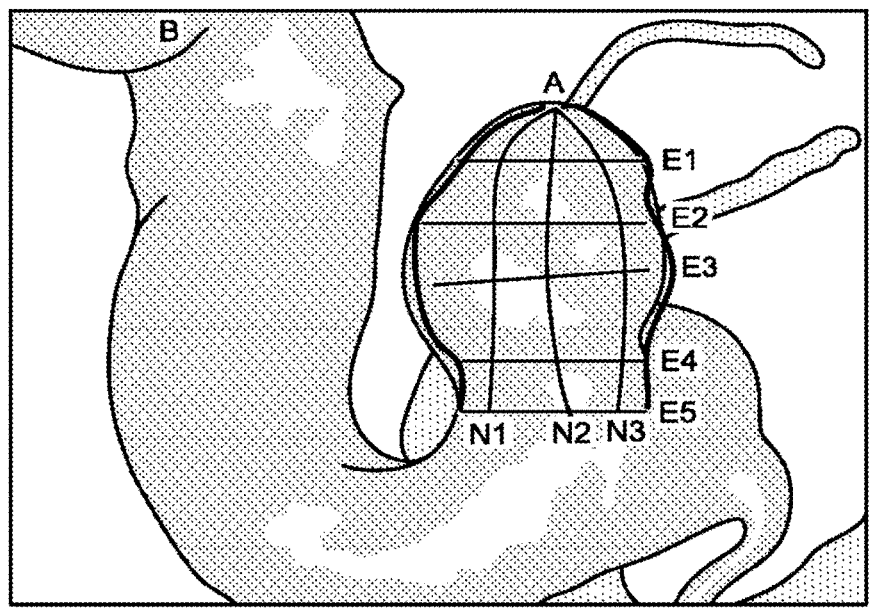
FIG. 7 is a schematic illustrating an example of the labels visually represented by the presenting function according to the first embodiment.

Once the first labels and the second labels are set based on the core line, the presenting function 244 displays the information indicating the first labels and the second labels at their respective positions in the X-ray image on the display 22a, based on the coordinate information of the brain aneurysm acquired by the acquiring function 246. In other words, the presenting function 244 presents information for identifying the positions of the respective feature points by presenting the information indicating the first labels and the second labels. FIG. 7 is a schematic illustrating an example of the labels visually presented by the presenting function 244 according to the first embodiment. For example, as illustrated in FIG. 7, the presenting function 244 enlarges the contrast image of the brain aneurysm having been selected from the contrast image of the brain artery via a contactless input, and displays the information representing the first labels of E1 to E5 and the second labels N1 to N3 at their respective positions in the enlarged contrast image.

In other words, the presenting function 244 displays the information representing the lines indicating the set planes and characters identifying the planes (E1 to E5 and N1 to N3) on the brain aneurysm in the contrast image, on the display 22a. The presenting function 244 presents the characters identifying the planes outside of the contour so that the characters do not overlap with the brain aneurysm, as illustrated in FIG. 7. For example, the presenting function 244 acquires the coordinates of the contour of the brain aneurysm from the coordinates of the brain aneurysm acquired by the acquiring function 246, and plots the characters to the coordinates outside of the acquired coordinates of the contour.

The presenting function 244 displays the labels based on the direction in which the brain aneurysm is displayed. In other words, the presenting function 244 visually presents the lines indicating the set planes and the characters identifying the planes, based on the direction in which the brain aneurysm is displayed in the display image having been generated from the volume data. For example, in FIG. 7, the first labels E1 to E5 and the second labels N1 to N3 are visually presented based on the direction in which the brain aneurysm is displayed, but the labels to be visually presented change depending on the direction in which the brain aneurysm is displayed.

Figure 8:
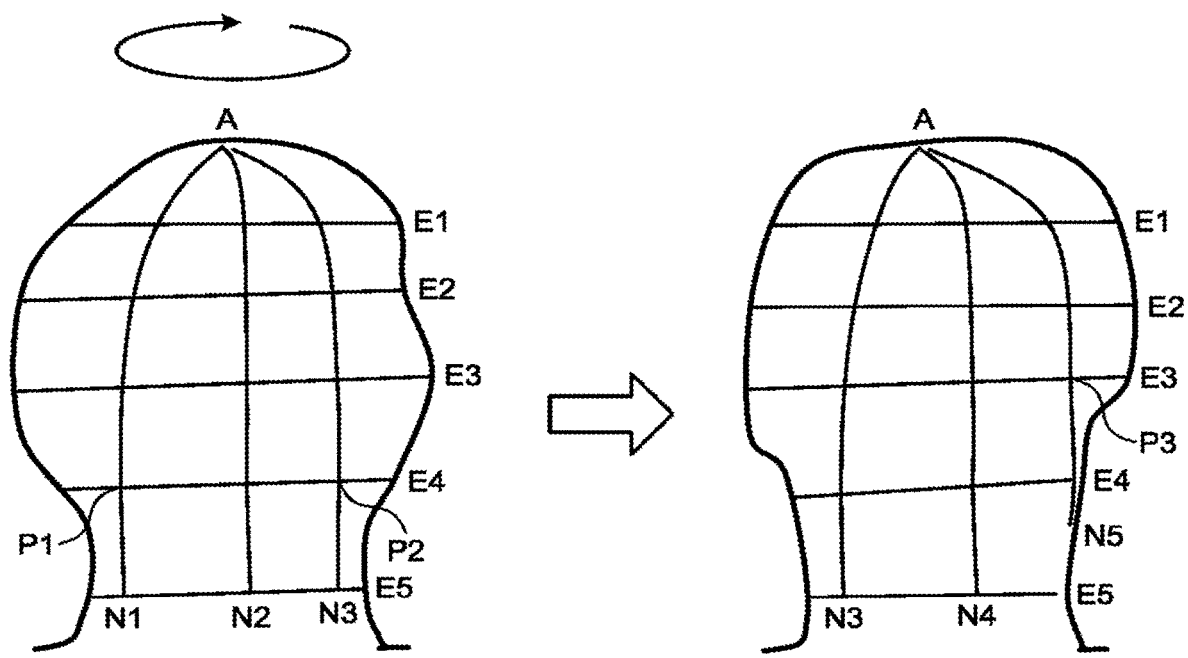
FIG. 8 is a schematic illustrating an example of a rotating view achieved by the presenting function according to the first embodiment.

For example, the presenting function 244 may provide a rotating view of the brain aneurysm and display different labels as the brain aneurysm is rotated. FIG. 8 is a schematic illustrating an example of a rotating view achieved by the presenting function 244 according to the first embodiment. FIG. 8 illustrates a rotating view of the brain aneurysm illustrated in FIG. 7. Illustrated in FIG. 8 is only the region corresponding to the brain aneurysm, but it is also possible to provide a rotating view including the blood vessel region. For example, the presenting function 244 provides a rotating view of a contrast image with the brain aneurysm, appended with the labels, on the display 22a, while rotating in a clockwise direction about the rotational axis at the core line L1 of the brain aneurysm selected with the terminal point label A, as illustrated in FIG. 8.

In other words, the labels shown for the brain aneurysm with a rotating view provided by the presenting function 244 change, as the brain aneurysm is rotated, as illustrated in FIG. 8. For example, as illustrated in FIG. 8, the second labels N1 to N3 are switched to the second labels N3 to N5 as the brain aneurysm is rotated. Here, the second labels N3 to N5 plotted to the positions facing the observable side (the front side) are shown, as the brain aneurysm is rotated. In this manner, the presenting function 244 displays a contrast image including the brain aneurysm appended with the labels for identifying positions.

The physician who is observing the contrast image via the display 22a can designate the position of the brain aneurysm using the labels on the contrast image displayed on the display 22a. For example, to designate a neck plane (a plane for identifying the region of a brain aneurysm) in order to measure the volume of the brain aneurysm, the physician can designate the neck plane by selecting the first labels and the second labels plotted to the brain aneurysm, via a contactless input such as an input of voice.

In other words, the receiving function 245 receives designating operation via a contactless input and the acquiring function 246 acquires the position information corresponding to the designating operation. Specifically, the receiving function 245 receives a contactless input related to a first label for selecting a position plotted along the direction of the core line, and a contactless input related to a second label for selecting a position plotted along the direction perpendicular to the direction of the core line. More specifically, the receiving function 245 receives a contactless input for selecting a plane with a specific first label among a plurality of planes with the first labels, and a contactless input for selecting a plane with a specific second label among a plurality of planes with the second labels. When the receiving function 245 receives an operation designating a plane such as the neck plane of the aneurysm described above, the receiving function 245 receives the contactless input related to the first label and the contactless input related to the second label a plurality of number of times. In other words, the receiving function 245 receives designating operations related to a plurality of positions (feature points) that delineate the neck plane.

An example will now be explained with reference to FIG. 8. For example, the presenting function 244 provides a rotating view of the brain aneurysm, as illustrated in FIG. 8. The physician then observes the rotating view of the brain aneurysm and verbally designates the feature points included in the neck plane, based on the labels displayed on the brain aneurysm. In other words, the physician designates the intersection points corresponding to the possible position of the neck plane, using the first labels and the second labels, from the intersection points in the grid lines plotted to the brain aneurysm with the lines indicating the respective planes. For example, the physician observes the rotating view of the brain aneurysm and verbally designates the "first label E4" and the "second label N1". Once the verbal designations of the "first label E4" and the "second label N1" are received, the receiving function 245 transmits the information of the combination of the "first label E4" and the "second label N1" to the acquiring function 246.

The acquiring function 246 then acquires the positions of the feature points in a target region defined by the position in the direction of the core line and the position in the direction perpendicular to the direction of the core line, with such positions being selected with the contactless inputs related to the first label and the second label, respectively. For example, the acquiring function 246 acquires position information "P1" that is the intersection point of the lines indicated by the "first label E4" and the "second label N1" received from the receiving function 245, based on the combination of these two labels. In other words, the acquiring function 246 acquires the coordinate information "P1" in the volume data.

To designate a neck plane is, positions of a plurality of points are designated depending on the shape of the brain aneurysm. Therefore, the receiving function 245 receives a designating operation of a combination of labels corresponding to a plurality of respective points, and the acquiring function 246 acquires the position information corresponding to the received positions. For example, it is assumed that the physician verbally designates the "first label E4" and the "second label N3", and the "first label E3" and the "second label N5", in addition to the "first label E4" and the "second label N1" mentioned above, while observing the rotating view of the brain aneurysm. Once the receiving function 245 receives the verbal designations of the "first label E4" and the "second label N3", and the "first label E3" and the "second label N5", the receiving function 245 transmits the information representing the combination of the "first label E4" and the "second label N3", and the information representing the combination of the "first label E3" and the "second label N5" to the acquiring function 246.

The acquiring function 246 acquires the positions of a plurality of respective feature points defined by a contactless input related to the first label and a contactless input related to the second label received a plurality of number of times by the receiving function 245, and acquires the position information of the plane defined by the acquired feature points. For example, based on the combination of the "first label E4" and the "second label N3" received from the receiving function 245, the acquiring function 246 acquires position information "P2" of the intersection point of the lines represented by these two labels. In other words, the acquiring function 246 acquires the coordinate information of "P2" in the volume data. Based on the combination of the "first label E3" and the "second label N5" received from the receiving function 245, the acquiring function 246 also acquires position information "P3" of the intersection point between the lines represented by the two labels. In other words, the acquiring function 246 acquires the coordinate information of "P3" in the volume data.

In this manner, once a plurality of pieces of coordinate information are acquired, the acquiring function 246 acquires the position information of the plane defined by these pieces of coordinate information, as the neck plane of the brain aneurysm. In other words, the acquiring function 246 assumes the plane passing through "P1", "P2", and "P3" as the neck plane, and acquires the position information (coordinate information) of the plane. The acquiring function 246 then transmits the acquired coordinate information of the plane to the measuring function 247.

Referring tack to FIG. 2, the measuring function 247 makes a measurement using the position information acquired by the acquiring function 246. For example, the measuring function 247 measures the volume of the brain aneurysm corresponding to the core line with the terminal point A, based on the coordinate information of the neck plane acquired by the acquiring function 246 and on the coordinate information of the voxels representing the brain aneurysm acquired by the acquiring function 246. In other words, the measuring function 245 measures the volume of the brain aneurysm delineated by the contour and the neck plane of the brain aneurysm.

In the manner described above, the X-ray angiography apparatus 1 according to the first embodiment can receive a designation of a position in an X-ray image via a contactless input such as a verbal input, and can perform a measurement process based on the received position. Therefore, the X-ray angiography apparatus 1 according to the first embodiment can reduce the burdens involved with contact-based inputs, and enables a user to make a designating operation easily.

Used in the embodiment described above is an example in which a rotating view of a three-dimensional contrast image is provided automatically. The embodiment is, however, not limited to such an example, and such a rotating view of a three-dimensional contrast image may be provided based on the result of a designating operation, for example. In such a case, the presenting function 244 provides a rotating view of the medical image based on a specific piece of identification information received by the receiving function 245. For example, if the receiving function 245 receives designations of the "first label E3" and the "second label N5", the presenting function 244 provides a rotating view of the brain aneurysm in such a manner that the "first label E3" and the "second label N5" received by the receiving function 245 are positioned at the center of the image.

Figure 9:
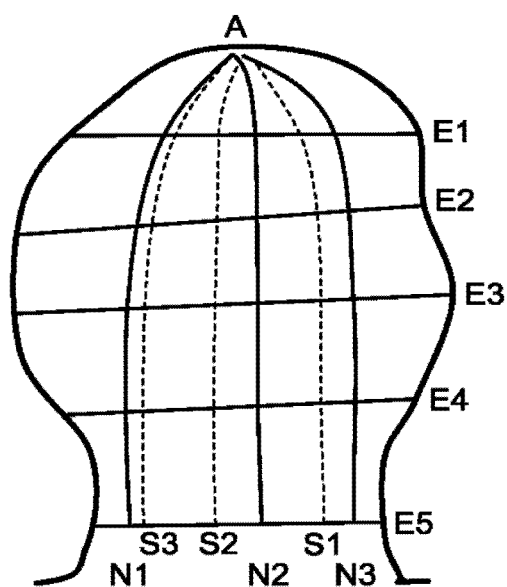
FIG. 9 is a schematic illustrating another example of the labels visually represented by the presenting function according to the first embodiment.

Furthermore, explained in the embodiment described above is an example in which the rear side of the brain aneurysm is displayed on the display 22a by providing a rotating view of the contrast image. The embodiment is, however, not limited to such an example, and the labels on the front side and those on the rear side may be displayed simultaneously in an X-ray image viewed from one direction, for example. FIG. 9 is a schematic illustrating another example of the labels visually represented by the presenting function 244 according to the first embodiment.

For example, among the second labels set to the brain aneurysm corresponding to the core line with the terminal point label A, the presenting function 244 displays the labels on the rear side in the direction in which the brain aneurysm is displayed as "S1", "S2", and "S3", respectively, in a manner distinguished from the second labels on the front side. The presenting function 244 also displays the lines representing the planes corresponding to the rear labels "S1", "S2" and "S3", in a manner distinguished from the lines representing the planes on the front side. When the rear labels are to be displayed simultaneously with the front labels, the presenting function 244 may also display the three-dimensional image in a manner allowing the rear side to be transparent and observable by changing the opacity of the image, on the display 22a.

As mentioned earlier, once the volume of the brain aneurysm is measured by the measuring function 247, the physician can determine the length of the coil to be used in coiling, based on the measurement result. In the X-ray angiography apparatus 1, the measuring function 247 may be controlled to identify some candidates of the coil to be used in coiling based on the measurement result, and the presenting function 244 may be controlled present the identified candidates to the physician. In such a case, for example, information associating the volume of an aneurysm with the type of coil to be used is stored in the memory 23 in advance, and the measuring function 247 determines the coil to be used based on the measurement result and the association information.

Furthermore, in the example described above, the labels are represented on the brain aneurysm, but the embodiment is not limited thereto. For example, the labels may be represented on the blood vessel region, in addition to the brain aneurysm. When coiling is to be carried out to a brain aneurysm, a stent is sometimes placed in order to prevent the coil from falling off from the brain aneurysm. In such a case, the physician makes a designating operation for designating the position at which the stent is placed. Because the X-ray angiography apparatus 1 receives a designating operation for such a stent placement via a contactless input, the user can make the designating operation easily.

Figure 10:
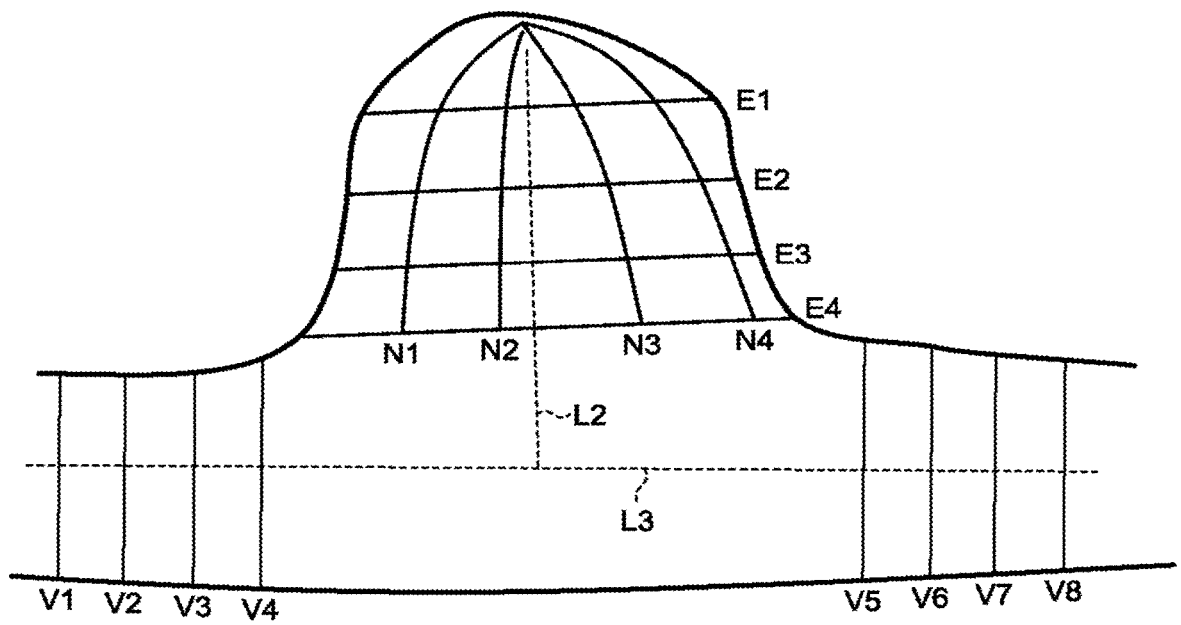
FIG. 10 is a schematic illustrating another example of the labels visually represented by the presenting function according to the first embodiment.
Figure 10:
Figure 10:
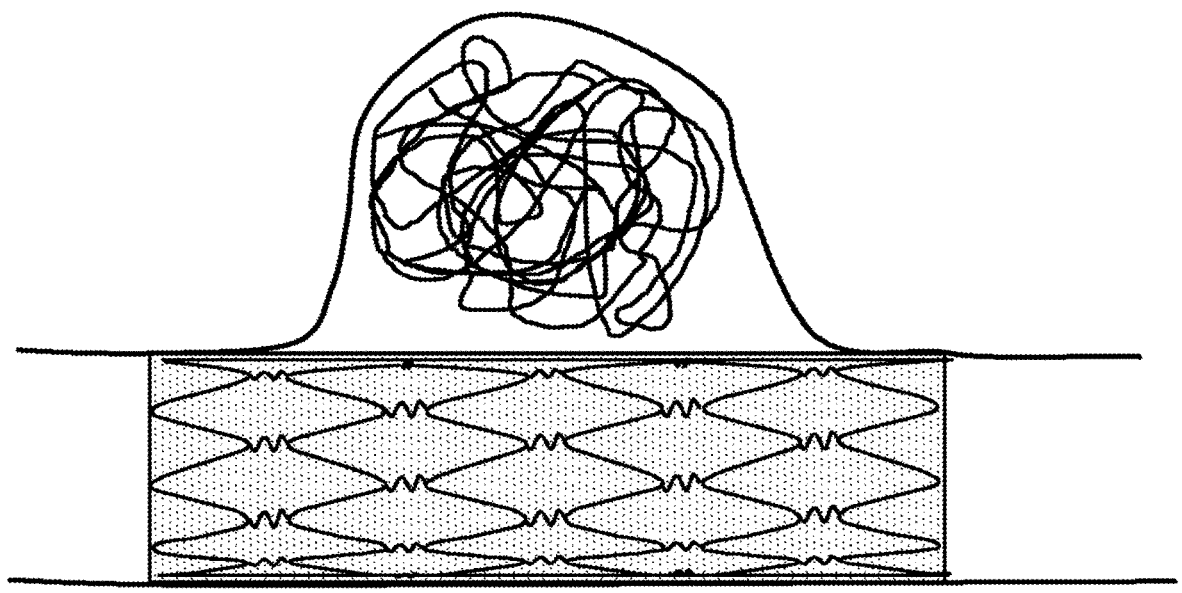

FIG. 10 is a schematic illustrating another example of the labels visually presented by the presenting function 244 according to the first embodiment. For example, as illustrated in the top diagram in FIG. 10, the setting function 243 sets first labels V1 to V8 that are based on a core line L3 of a blood vessel, in addition to the first labels E1 to E4 and the second labels N1 to N4 that are based on the core line L2 of the brain aneurysm. The presenting function 244 displays a contrast image in which the first labels V1 to V8, as well as the first label E1 to E4 and the second labels N1 to N4, are represented on the display 22a, as illustrated in the top diagram in FIG. 10.

In addition to receiving the designating operations of the first labels E1 to E4 and the second labels N1 to N4, which are based on the core line L2 of the brain aneurysm, via a contactless input, the receiving function 245 receives a designating operation of the first labels V1 to V8, which are based on the core line L3 of the blood vessel, via a contactless input. In other words, the physician makes contactless inputs for designating the neck plane of the brain aneurysm and contactless inputs for designating the position at which the stent is placed.

For example, the physician verbally makes a designating operation for designating one of the first labels V1 to V4, and a designating operation for designating one of the first labels V5 to V8, in addition to the above-described designating operation for designating a neck plane. To explain the operation using an example, the physician verbally designates the first labels "V2" and "V6". The receiving function 245 then transmits the first labels "V2" and "V6" to the acquiring function 246. The acquiring function 246 acquires the coordinate information of the first labels "V2" and "V6" in the volume data, and sends the coordinate information to the measuring function 247. The measuring function 247 determines the length of the stent by measuring the length between these coordinates (designated section), based on the coordinate information received from the acquiring function 246. The measuring function 247 also determines, by measuring the diameter of the blood vessel in the designated section received from the acquiring function 246 based on the volume data, the diameter of the stent based on the measurement result.

In this manner, the physician can carry out coiling using a type of coil suitable for the treatment of the brain aneurysm, as illustrated in the bottom drawing in FIG. 10, and place a stent suitable for preventing the coil from falling off. Such a procedure is carried out to a brain aneurysm with a wider bottom (not very constricted), an example of which is illustrated in FIG. 10. In the top drawing in FIG. 10, the lines indicating the planes intersecting perpendicularly to the core line L3 are visually presented as the first labels V1 to V8, which are based on the core line L3 of the blood vessel, but the embodiment is not limited to such an example, and points may be displayed at corresponding positions on the core line L3, for example. In such a case, the setting function 243 sets points (feature points) to the core line L3 at predetermined intervals.

Figure 11:
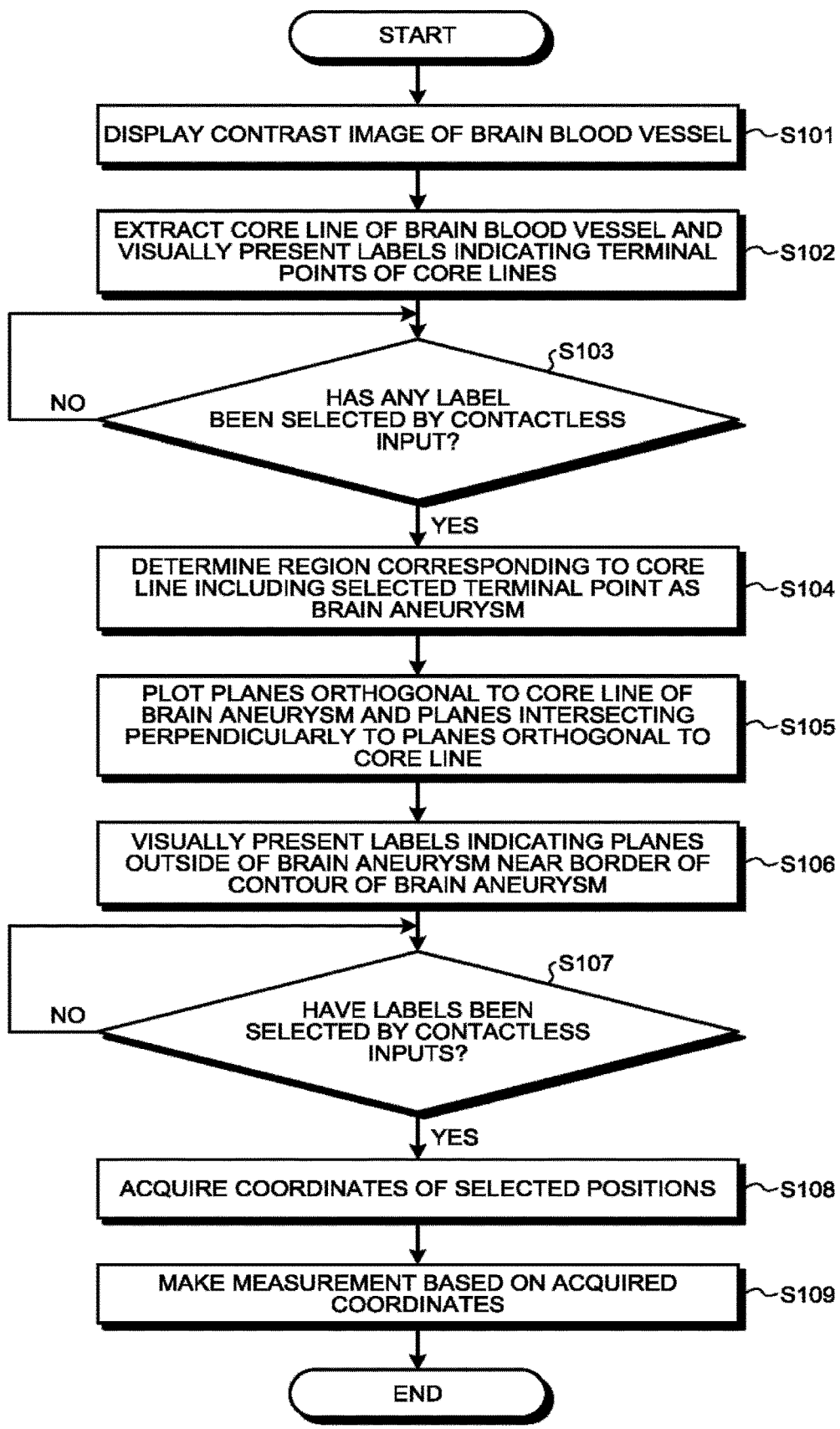
FIG. 11 is a flowchart illustrating a process performed in the X-ray angiography apparatus according to the first embodiment.

A process performed in the X-ray angiography apparatus 1 according to the first embodiment will now be explained with reference to FIG. 11. FIG. 11 is a flowchart illustrating the process performed in the X-ray angiography apparatus according to the first embodiment. Steps S101, and S104 to S106 illustrated in FIG. 11 are steps implemented by causing the processing circuitry 24 to read a computer program corresponding to the presenting function 244 from the memory 3, and to execute the computer program. Step S102 is a step implemented by causing the processing circuitry 24 to read computer programs corresponding to the extracting function 242, the setting function 243, and the presenting function 244 from the memory 23, and to execute the computer programs. Steps S103 and S107 are steps implemented by causing the processing circuitry 24 to read a computer program corresponding to the receiving function 245 from the memory 23, and to execute the computer program. Step S108 is a step implemented by causing the processing circuitry 24 to read a computer program corresponding to the acquiring function 246 from the memory 23, and to execute the computer program. Step S109 is a step implemented by causing the processing circuitry 24 to read a computer program corresponding to the measuring function 247 from the memory 23, and to execute the computer program.

At Step S101, the processing circuitry 24 causes the display 22a to display a contrast image of a brain blood vessel. At Step S102, the processing circuitry 24 extracts the core line of the brain blood vessel, and visually presents the terminal point labels indicating the respective terminal points of the core line on the contrast image. At Step S103, the processing circuitry 24 determines whether any terminal point label has been selected by a contactless input. If a terminal point label has been selected by a contactless input (Yes at Step S103), at Step S104, the processing circuitry 24 determines the region corresponding to the core line including the selected terminal point as the brain aneurysm. Until a terminal point label is selected by a contactless input, the X-ray angiography apparatus 1 is kept waiting (No at Step S103).

At Step S105, the processing circuitry 24 plots some planes orthogonal to the core line of the brain aneurysm, and some planes intersecting perpendicularly to the planes orthogonal to the core line. At Step S106, the processing circuitry 24 visually presents the labels indicating these planes outside of the brain aneurysm near the border of the contour of the brain aneurysm. At Step S107, the processing circuitry 24 determines whether some labels have been selected by contactless inputs. If some labels have been selected by contactless inputs (Yes at Step S107), at Step 5108, the processing circuitry 24 acquires the coordinates of the selected position. Until some labels are selected by contactless inputs, the X-ray angiography apparatus 1 is kept waiting (No at Step S107). At Step S109, the processing circuitry 24 makes a measurement based on the acquired coordinates.

As described above, according to the first embodiment, the extracting function 242 extracts a core line of the region of interesting the medical image collected from the subject. The setting function 243 sets feature points of the region of interest based on the core line and the contour of the region of interest. The presenting function 244 presents identification information for identifying the positions of the set feature points. The receiving function 245 receives a contactless input for selecting a specific piece of identification information from a plurality of pieces of identification information presented in the medical image. The acquiring function 246 then acquires the position of the feature point having the corresponding identification information in the medical image, based on the specific piece of identification information for which a contactless input is received. In this manner, the X-ray angiography apparatus 1 according to the first embodiment can receive a designating operation designating a position in the medical image via a contactless input such as an input via voice, so that the user can make a designating operation easily.

Furthermore, according to the first embodiment, the setting function 243 sets the feature points based on the positions plotted along the direction of the core line of the region of interest and the positions plotted along the direction perpendicular to the direction of the core line of the region of interest. The presenting function 244 presents the first labels for identifying the positions plotted along the direction of the core line of the region of interest and the second labels for identifying the positions plotted along the direction perpendicular to the direction of the core line of the region of interest, to the corresponding positions in the region of interest. The receiving function 245 receives a contactless input related to the first label for selecting a position plotted along the direction of the core line, and a contactless input related to the second label for selecting a position plotted along the direction perpendicular to the direction of the core line. The acquiring function 246 acquires the position of the feature point defined by the position plotted along the direction of the core line and the position plotted along the direction perpendicular to the direction of the core line in the region of interest, such positions being selected with the contactless inputs related to the first label and the second label, respectively. Therefore, the X-ray angiography apparatus 1 according to the first embodiment enables an operator to designate one of the positions presented as a grid in the medical image, so that the operator is allowed to make a designating operation for a more specific position, and as a result, highly precise measurements can be achieved.

Furthermore, according to the first embodiment, the extracting function 242 extracts a core line of a region of interest from a three-dimensional medical image collected from a subject. The setting function 243 sets he feature points based on the first planes that are plotted perpendicularly to the core line of the region of interest and the second planes that are plotted perpendicularly to the first planes and passing the core line. The presenting function 244 presents the labels for identifying the first planes that are plotted perpendicularly to the core line as the first labels, and the labels for identifying the second planes that are plotted perpendicularly to the first planes and pass the core line as the second labels. The receiving function 245 receives a contactless input for selecting a plane with a specific first label from the planes with the first labels, and a contactless input for selecting a plane with a specific second label from the planes with the second labels. The acquiring function 246 acquires the positions of the feature points defined by the plane with the specific first label and the plane with the specific second label, selected via the contactless inputs. Therefore, the X-ray angiography apparatus 1 according to the first embodiment can use the same labels regardless of the shape of the region of interest, and can achieve highly precise measurements.

Furthermore, according to the first embodiment, the presenting function 244 presents terminal point labels for identifying a terminal point of the core line at a position corresponding to the region of interest. The receiving function 245 receives a contactless input for selecting a specific terminal point label from the terminal point labels presented in the region of interest. With respect to the core line having the terminal point with a terminal point label having been selected, the presenting function 244 presents the first labels and the second labels in the region of interest. The receiving function 245 receives a contactless input related to the first label and a contactless input related to the second label a plurality of number of times. The acquiring function 246 acquires the position information of a plurality of positions defined by the contactless inputs related to the first labels and the contactless inputs related to the second labels, received a plurality of number of times by the receiving function 245, and acquires the position information of the plane defined by the acquired pieces of position information. Therefore, the X-ray angiography apparatus 1 according to the first embodiment enables an operator o designate a neck plane of an aneurysm accurately.

Furthermore, according to the first embodiment, the presenting function 244 presents a terminal point label for a terminal point the distance of which from a branch is equal to or shorter than a predetermined threshold among the terminal points of the core line of the region of interest. Therefore, the X-ray angiography apparatus 1 according to the first embodiment can assign a label only to the region that is highly likely to be a brain aneurysm.

Furthermore, according to the first embodiment, the presenting function 244 presents a terminal point label for a terminal point of a region having a diameter that is equal to or larger than a predetermined threshold. Therefore, the X-ray angiography apparatus 1 according to the first embodiment can assign a label to the inside of an image, taking the likelihood of developing the region having a brain aneurysm into consideration.

Furthermore, according to the first embodiment, the presenting function 244 provides a rotating view of the medical image, based on a specific piece of identification information received by the receiving function 245. Therefore, the X-ray angiography apparatus 1 according to the first embodiment enables an operator to make a designation easily, even when a plane is designated by the operator in the image.

Furthermore, according to the first embodiment, the measuring function 247 makes a measurement using the position information acquired by the acquiring function 246. Therefore, the X-ray angiography apparatus 1 according to the first embodiment enables a measurement to be made using the position information designated by a designating operation via a contactless input, such as an input of voice.

Furthermore, according to the first embodiment, the receiving function 24.5 receives an input using at least one of voice and eve gaze of the operator as the contactless input. Therefore, the X-ray angiography apparatus 1 according to the first embodiment enables an operator to make a designating operation easily without requiring an operation of an input device, for example.

Second Embodiment

Explained in the embodiment described above is an example in which volume data is collected, and the labels are visually represented to a three-dimensional image generated from the collected volume data. Explained now in a second embodiment is an example in which the label is visually represented to a two-dimensional image. In the X-ray angiography apparatus 1 according to the second embodiment, the processes executed by the setting function 243 and the presenting function 244 are different from those executed in the X-ray angiography apparatus 1 according to the first embodiment. This difference will be mainly explained below.

Figure 12A:
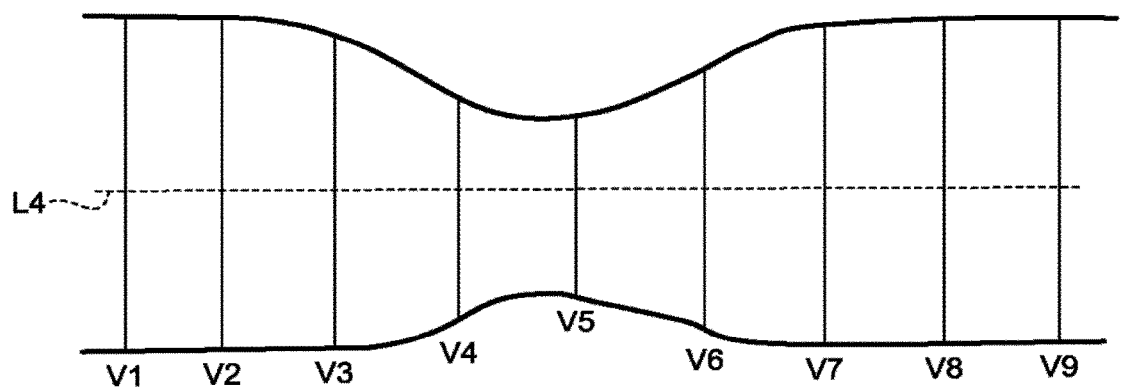
FIG. 12A is a schematic illustrating an example of labels visually presented by a presenting function according to a second embodiment.

The setting function 243 according to the second embodiment sets the labels for identifying positions based on a core line of a region of interest in a two-dimensional image. The presenting function 244 according to the second embodiment then visually presents the set labels onto the two-dimensional image. FIG. 12A is a schematic illustrating an example of the labels visually represented by the presenting function 244 according to the second embodiment. As illustrated in FIG. 12A, the presenting function 244 displays a two-dimensional image of a blood vessel with first labels V1 to V9 visually represented as lines that intersect perpendicularly to a core line L4 of the blood vessel at equal intervals. In this manner, for example, a physician can designate the position at which a stent is to be placed with respect to a stenosis of the blood vessel by verbally designating the first labels V1 to V9 that are visually presented via contactless inputs. As a result, the X-ray angiography apparatus 1 can determine the size of the stent to be placed, based on the designated first labels.

Figure 12B:
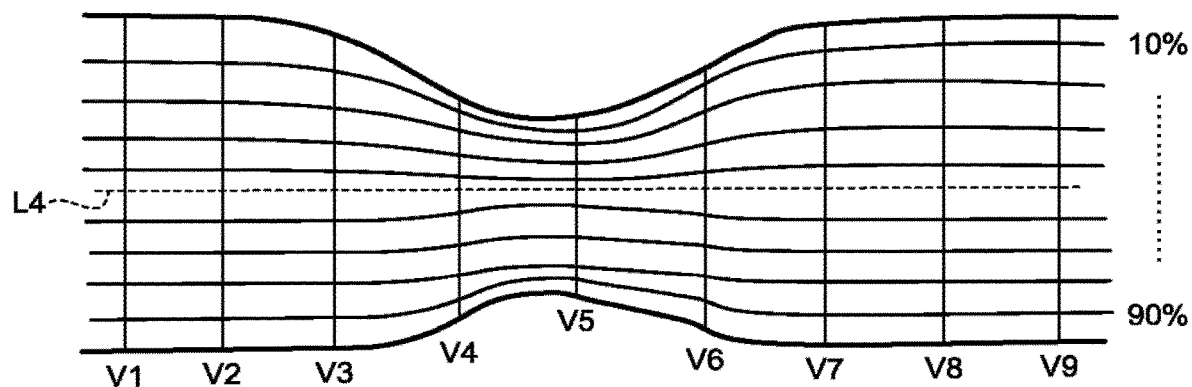
FIG. 12B is a schematic illustrating an example of the labels visually represented by the presenting function according to the second embodiment.

The presenting function 244 can also set the second labels for identifying the positions plotted along the direction perpendicular o the direction of the core line, even when the labels are to be set to a two-dimensional image. FIG. 12B is a schematic illustrating an example of the labels visually represented by the presenting function 244 according to the second embodiment. As illustrated in FIG. 122, the presenting function 244 can visually present the second labels indicating positions plotted along the direction perpendicular to the core line L4, in addition to the first labels V1 to V9 represented as the lines that intersect perpendicularly to the core line L4 of the blood vessel. The presenting function 244 according to the second embodiment assigns the labels at the positions of the blood vessel equally divided along the direction perpendicular to the core line L4, as the second labels, as illustrated in FIG. 12B. For example, the presenting function 244 assigns the second label to every position at an increment of "10%", in the thickness direction of the blood vessel.

Such a label assignment may also be used in coordinate corrections, for example. To explain this using an example, an operator can make a designating operation using a label to correct the coordinates of the core line when there is some error resulting from a metal artifact, for example, in the core line extracted from the two-dimensional image. In such a case, the physician may visually identify a blood vessel region and the artifact region in the image, determine the position of the core line considered to be appropriate, based on the blood vessel region having been visually identified, and correct the coordinates of the core line by designating the determined position via a contactless input using the label. For example, the presenting function 244 displays a two-dimensional image in which the position of the core line has been corrected to a position designated by the physician.

As described above, according to the second embodiment, the presenting function 244 sets the labels for identifying positions based on a core line of a region of interest in a two-dimensional image, and visually presents the set labels in the two-dimensional image. Therefore, the X-ray angiography apparatus 1 according to the second embodiment enables an operator to make a designating operation in various types of medical images via a contactless input.

Third Embodiment

The first and the second embodiments are explained above, but embodiments different from those are still possible, in addition to the first and the second embodiments described above.

Explained in the embodiments described above is an example in which a core line of a tubular structure is used as a reference line of a region of interest in a medical image collected from a subject. The embodiments are, however, not limited to such an example and any other various lines may be used as the reference. For example, a line of sight in an endoscopic image may also be used as a reference line of a region of interest in a medical image collected from a subject. Explained below is an example in which the line of light in an endoscopic image is used as a reference line.

For example, the setting function 243 according to a third embodiment sets positions in a lumen in the direction of a line of sight. The presenting function 244 according to the third embodiment presents pieces of identification information for identifying positions plotted along the direction of the line of sight in the lumen at their corresponding positions in the lumen. The receiving function 245 according to the third embodiment receives a contactless input related to the identification information for selecting a position plotted along the direction of the line of sight. The acquiring function 246 according to the third embodiment then acquires the position plotted along the direction of the line of sight, selected by the contactless input related to the identification information.

Figure 13A:
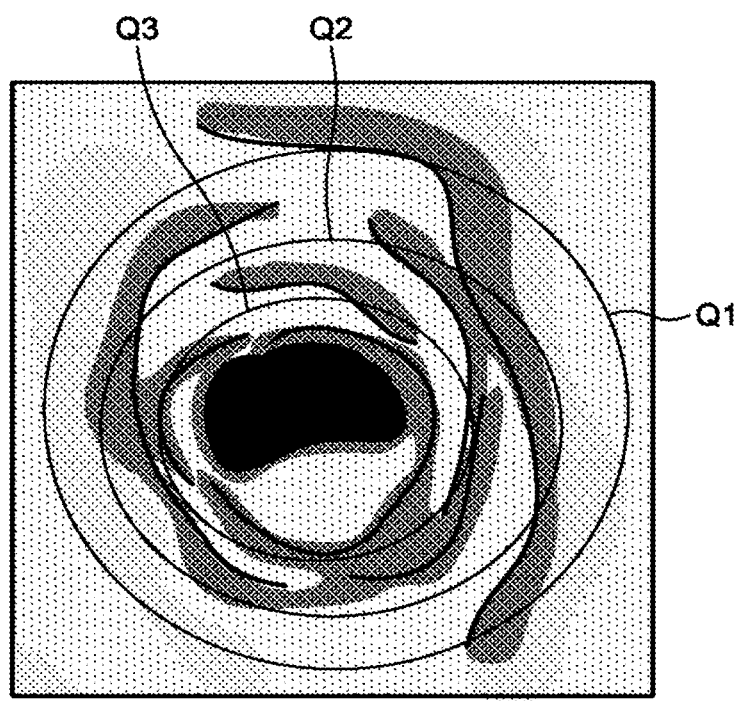
FIG. 13A is a schematic illustrating an example of labels visually presented by a presenting function according to a third embodiment.

In other words, the setting function 243 sets the labels to positions plotted along the direction of the line of sight in the lumen. The presenting function 244 then visually presents the set labels in the endoscopic image. FIG. 13A is a schematic illustrating an example of the labels visually represented by the presenting function 244 according to the third embodiment. For example, the presenting function 244 presents labels Q1, Q2, and Q3, for example, in the endoscopic image, as illustrated in FIG. 13A.

Setting of the labels in an endoscopic image will now be explained. Explained below is an example in which a virtual endoscopic image is generated using volume data, and the labels are set to the generated virtual endoscopic image. In such a case, the setting function 243 acquires the information of the position of the point of view and the line of sight that are used when the virtual endoscopic image is generated from the volume data. The setting function 243 then sets the labels, based on the acquired position of the point of view and line of sight.

Figure 13B:
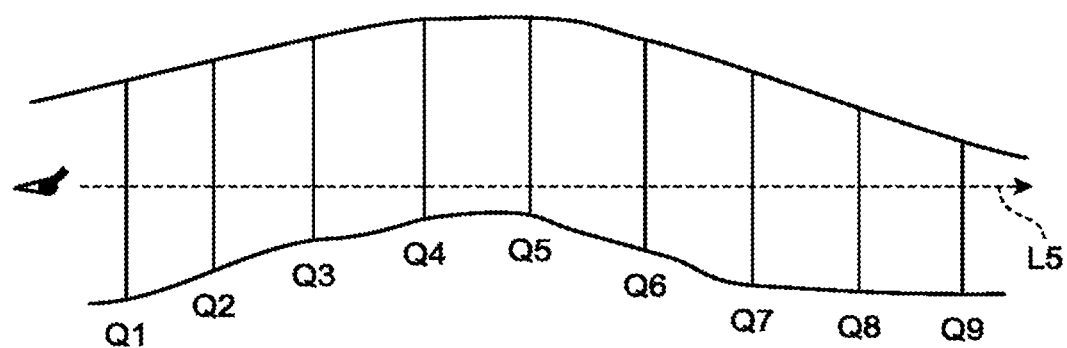
FIG. 13B is a schematic for explaining an example of how the labels are set by a setting function according to the third embodiment.

FIG. 13B is a schematic for explaining an example of how the labels are set by the setting function according to the third embodiment. FIG. 13B illustrates a cross section of the longitudinal axis of the lumen illustrated in FIG. 13A. For example, the setting function 243 acquires the position of the point of view and the line of sight used in generating the virtual endoscopic image illustrated in FIG. 13A, and sets the labels of Q1 to Q9 along the direction of a line of sight L5 from the point of view, as illustrated in FIG. 13B. The setting function 243 sets the labels to positions of the planes that are perpendicular to the line of sight and intersect with the wall of the lumen. For example, the setting function 243 plots planes perpendicular to the line of sight to the positions at predetermined distances from the point of view along the line of sight, and sets the labels Q1 to Q9 to the positions at which the plotted planes intersect with the wall of the lumen (the voxel intersecting with the planes in the volume data).

In other words, the setting function 243 sets a plurality of ring-like labels the lumen with a tubular structure.

The presenting function 244 causes the display 22a to display the virtual endoscopic image in which the labels set to the corresponding positions of the virtual endoscopic image are visually presented, for example. Specifically, the presenting function 244 displays an image with the labels visually presented in the virtual endoscopic image at positions corresponding to the positions to which the labels are set in the volume data, on the display 22a, for example. In this manner, for example, the physician can designate a position in the lumen by designating the visually presented labels Q1 to Q9 by voice.

Explained in the embodiments described above is an example in which the X-ray angiography apparatus 1 is used as an example of the medical image diagnostic apparatus. However, the embodiments are not limited to such an example, and the process described above may be executed by any other modality, such as an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus which is an integration of an SPECT apparatus and an X-ray CT apparatus, or a PET-CT apparatus which is an integration of a PET apparatus and an X-ray CT apparatus.

Furthermore, explained in the embodiments described above is an example in which the region of interest is an aneurysm or a stenosis in a blood vessel in the brain. The embodiments are, however, not limited to such an example, and the region of interest may be a stenosis in a blood vessel in a lower limb or a neck, a stenosis in a coronary artery, or a tumor.

Furthermore, explained in the embodiments described above is an example in which voice is input as a contactless input. The embodiments are, however, not limited to such an example, and an eye care may be used as the contactless input, for example. In such a case, for example, the receiving function 245 receives the label visually presented at a position pointed by an eye gaze on the display 22a from the input device 300, as a label designated via a contactless input.

Furthermore, explained in the embodiments described above is an example in which the characters for identifying the planes are visually presented in the medical image. The embodiments are, however, not limited to such an example, and the characters may be assigned to the intersection points of the lines representing the planes, for example.

Furthermore, explained in the embodiments described above is an example in which the terminal point labels assigned to a core line is presented; a designating operation for designating the position of a brain aneurysm (an operation of selecting the aneurysm in the image) is then received; and the labels for identifying respective positions in the brain aneurysm are presented. The embodiments are, however, not limited to such an example and only the labels for identifying positions in the brain aneurysm may be presented, for example.

Figure 14:
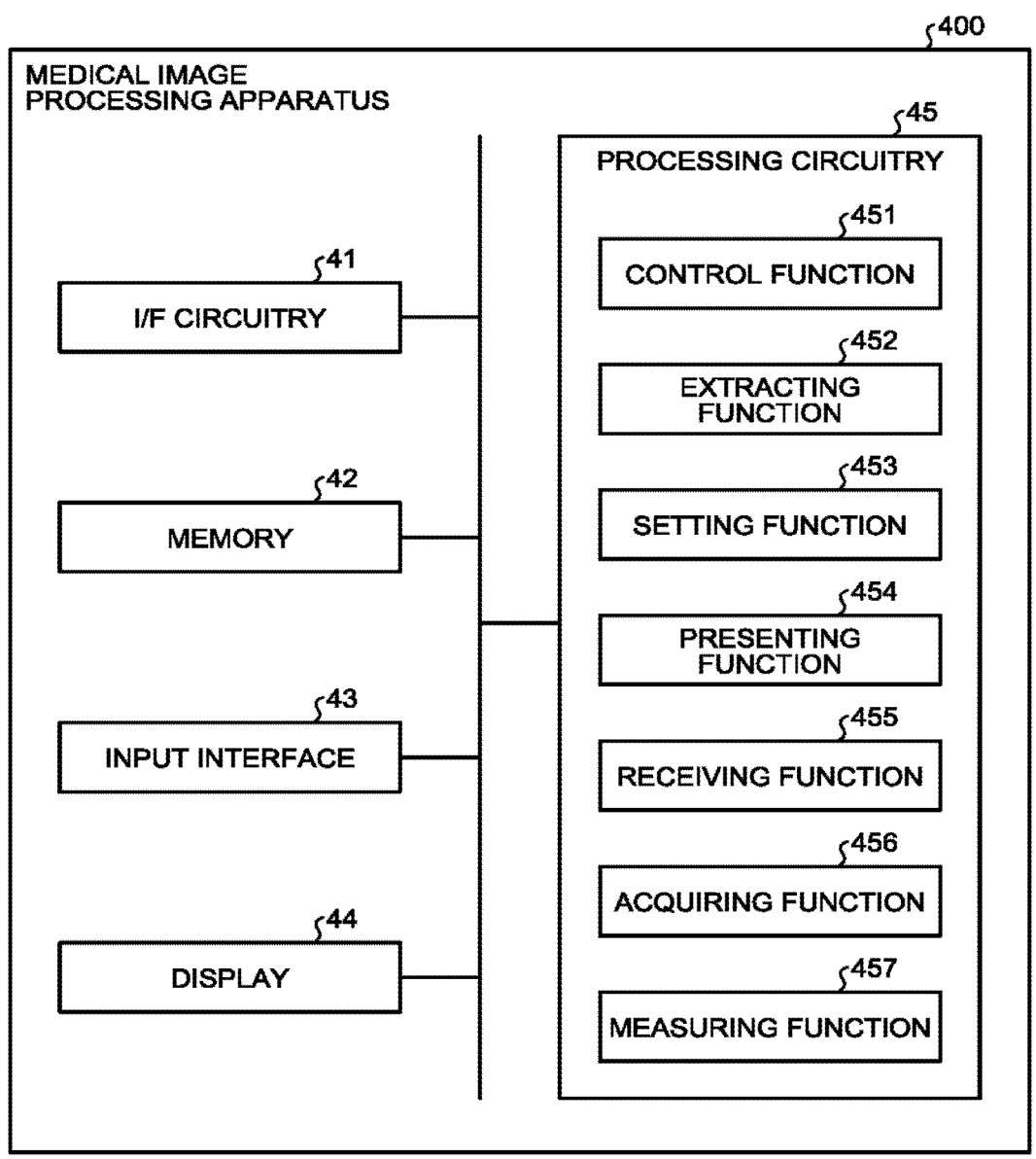
FIG. 14 is a schematic illustrating an example of a configuration of a medical image processing apparatus according to the third embodiment.

Furthermore, explained in the embodiments described above is an example in which the process is performed by a medical image diagnostic apparatus. The embodiments are, however, not limited to such an example and the process may be performed by a medical image processing apparatus, for example. FIG. 14 is a schematic illustrating an example of a configuration of a medical image processing apparatus 400 according to the third embodiment.

The medical image processing apparatus 400 is an information processing apparatus such as a workstation, and includes interface (I/F) circuitry 41, a memory 42, an input interface 43, a display 44, and processing circuitry 45, as illustrated in FIG. 14. The medical image processing apparatus 400 is installed in the examination room R1, for example.

The I/F circuitry 41 is connected to the processing circuitry 45 and controls the transfer and the communication of various data with a medical image diagnostic apparatus, such as the X-ray angiography apparatus 1, or an image storage apparatus, connected over a network. The I/F circuitry 41 is implemented with a network card, a network adapter, or a network interface controller (NIC), for example.

The memory 42 is connected to the processing circuitry 45 and stores therein various types of data. For example, the memory 42 is implemented with a random access memory (RAM), a semiconductor memory device such as a flash memory, a hard disk, or an optical disc. The memory 42 stores therein medical image data received from a medical image diagnostic apparatus such as the X-ray angiography apparatus 1, or an image storage apparatus.

The input interface 43 is connected to the processing circuitry 45, converts an input operation received from the operator into an electrical signal, and outputs the electrical signal to the processing circuitry 45. For example, the input interface 43 is implemented with a trackball, a switch button, a mouse, a keyboard, or a touch panel.

The display 44 is connected to the processing circuitry 45 and displays various types of information and various image data output from the processing circuitry 45. The display 44 is implemented with a liquid crystal monitor, a cathode ray tube (CRT) monitor, or a touch panel, for example.

The processing circuitry 45 controls h elements of the medical image processing apparatus 400, in response to an input operation received from the operator via the input interface 43. For example, the processing circuitry 45 is implemented with a processor. The processing circuitry 45 stores the medical image data output from the I/F circuitry 41 in the memory 42. The processing circuitry 45 also reads the medical image data from the memory 42, executes various image processing, and displays the medical image data on the display 44.

The processing circuitry 45 executes a control function 451, an extracting function 452, a presenting function 454, a receiving function 455, an acquiring function 456, and a measuring function 45i, as illustrated in FIG. 14. The control function 451 controls the entire medical image processing apparatus 400. The extracting function 452 performs the same process as that performed by the extracting function 242 described above. The presenting function 454 performs the same process as that performed by the presenting function 244 described above. The receiving function 455 performs the same process as that performed by the receiving function 245 described above. The acquiring function 456 performs the same process as that performed by the acquiring function 246 described above. The measuring function 457 performs the same process as that performed by the measuring function 247 described above.

In the medical image processing apparatus 400 illustrated in FIG. 14, these processing functions are stored in the memory 42 as computer-executable programs. The processing circuitry 45 is a processor for implementing the function corresponding to each of the computer programs by reading and executing the corresponding computer program from the memory 42. In other words, the processing circuitry 45 having read the computer program will have the function corresponding to the read computer program.

Explained in the embodiments described above is an example in which a single processing circuitry (the processing circuitry 24 and the processing circuitry 45) implements the corresponding processing functions, but the embodiments are not limited thereto. For example, the processing circuitry 24 and the processing circuitry 45 may be provided as a combination of a plurality of independent processors, and the processing functions may be implemented by causing each of the processors to execute corresponding computer programs. Each of the processing functions provided to the processing circuitry 24 and the processing circuitry 45 may be implemented by integrating the processing functions into a single processing circuit, or distributing the processing functions to a plurality of processing circuits, as appropriate.

Furthermore, the term "processor" used in the explanation of the embodiments above means a circuit such as a central processing unit (CPU), a graphics processing unit (GPU), an application specific integrated circuit (ASIC), a programmable logic device (such as a simple programmable logic device (SPLD)), a complex programmable logic device (CPLD)), or a field programmable gate array (FPGA). Instead of storing the computer programs in the memory, the computer programs may be embedded directly into the processor circuit. In such a configuration, the processor implements the functions by reading the computer programs embedded in the circuit, and executing the computer programs. Furthermore, each of the processors according to the embodiments may be provided as a combination of a plurality of independent circuits serving as one processor, and the combination may be caused to implement the functions, without limitation to the configuration in which one processor is provided as one single circuit.

As explained above, according to the first to the third embodiments, an operator can make a designating operation easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic apparatus comprising processing circuitry configured to:
   extract a core line of a region of interest having a tubular structure in a medical image collected from a subject;
   set a plurality of points based on positions plotted along a direction of the core line of the region of interest, and positions plotted along a direction perpendicular to the direction of the core line of the region of interest;
   indicate pieces of first identification information for identifying the positions plotted along the direction of the core line of the region of interest, and pieces of second identification information for identifying the positions plotted along the direction perpendicular to the direction of the core line of the region of interest, at corresponding positions in the region of interest;
   receive a contactless input related to the first identification information for selecting a position plotted along the direction of the core line, and a contactless input related to the second identification information for selecting a position plotted along the direction perpendicular to the direction of the core line; and acquire a position of a point defined by the position plotted along the direction of the core line and selected by the contactless input related to the first identification information, and defined by the position plotted along the direction perpendicular to the direction of the core line and selected by the contactless input related to the second identification information.

2. The medical image diagnostic apparatus according to claim 1, wherein the processing circuitry is configured to:
    extract a core line of a region of interest included in a three-dimensional medical image collected from the subject;
    set the plurality of points based on a plurality of first planes that are plotted perpendicularly to the core line of the region of interest and a plurality of second planes that are plotted perpendicularly to the first planes and passing the core line;
    indicate pieces of identification information for identifying the first planes, as the first identification information, and indicate pieces of identification information for identifying the second planes, as the second identification information;
    receive a contactless input for selecting a specific first plane from the first planes, and a contactless input for selecting a specific second plane from the second planes; and
    acquire a position of a point defined by the specific first plane and the specific second plane selected by the contactless inputs.

3. The medical image diagnostic apparatus according to claim 2, wherein the processing circuitry is also configured to:
    indicate pieces of terminal point identification information for identifying terminal points of the core line, at corresponding positions in the region of interest;
    receive a contactless input for selecting a specific piece of terminal point identification information from the pieces of terminal point identification information indicated at the corresponding positions in the region of interest;
    indicate the first identification information and the second identification information for a core line with a terminal point corresponding to the selected terminal point identification information, in the region of interest;
    receive a contactless input related to the first identification information and a contactless input related to the second identification information, a plurality of number of times; and
    acquire positions of a plurality of points each of which is defined by the contactless input related to the first identification information and the contactless input related to the second identification information, the contactless input having been received a plurality of number of times, and acquire position information of a plane defined by the acquired positions of the points.

4. The medical image diagnostic apparatus according to claim 3, wherein the processing circuitry is configured to indicate the terminal point identification information for a terminal point a distance of which to a branch is equal to or shorter than a predetermined threshold, among the terminal points of the core line of the region of interest.

5. The medical image diagnostic apparatus according to claim 3, wherein the processing circuitry is configured to indicate the terminal point identification information for a terminal point included in a region having a diameter that is equal to or larger than a predetermined threshold, in the region of interest.

6. The medical image diagnostic apparatus according to claim 1, wherein
    the processing circuitry is further configured to:
        set positions along the line of sight in the interior cavity of the region of interest having the tubular structure;
        indicate pieces of identification information for identifying the positions along the line of sight in the interior cavity, at corresponding positions in the interior cavity;
        receive a contactless input related to the identification information for selecting a position along the line of sight; and
        acquire a position along the line of sight selected by the contactless input related to the identification information.

7. The medical image diagnostic apparatus according to claim 1, wherein the processing circuitry is configured to provide a rotating view of the medical image, based on a received specific piece of identification information.

8. The medical image diagnostic apparatus according to claim 1, wherein the processing circuitry is also configured to make a measurement using acquired position information.

9. The medical image diagnostic apparatus according to claim 1, wherein the processing circuitry is configured to receive an input via at least one of voice and eye gaze of an operator, as the contactless input.

10. A medical image processing apparatus comprising processing circuitry configured to:
    extract a core line of a region of interest having a tubular structure in a medical image collected from a subject;
    set a plurality of points based on positions plotted along a direction of the core line of the region of interest, and positions plotted along a direction perpendicular to the direction of the core line of the region of interest;
    indicate pieces of first identification information for identifying the positions plotted along the direction of the core line of the region of interest, and pieces of second identification information for identifying the positions plotted along the direction perpendicular to the direction of the core line of the region of interest, at corresponding positions in the region of interest;
    receive a contactless input related to the first identification information for selecting a position plotted along the direction of the core line, and a contactless input related to the second identification information for selecting a position plotted along the direction perpendicular to the direction of the core line; and
    acquire a position of a point defined by the position plotted along the direction of the core line and selected by the contactless input related to the first identification information, and defined by the position plotted along the direction perpendicular to the direction of the core line and selected by the contactless input related to the second identification information.

11. The medical image processing apparatus according to claim 10, wherein the processing circuitry is configured to:
    extract a core line of a region of interest included in a three-dimensional medical image collected from the subject;
    set the plurality of points based on a plurality of first planes that are plotted perpendicularly to the core line of the region of interest and a plurality of second planes that are plotted perpendicularly to the first planes and passing the core line;

indicate pieces of identification information for identifying the first planes, as the first identification information, and indicate pieces of identification information for identifying the second planes, as the second identification information;

receive a contactless input for selecting a specific first plane from the first planes, and a contactless input for selecting a specific second plane from the second planes; and acquire a position of a point defined by the specific first plane and the specific second plane selected by the contactless inputs.

12. The medical image processing apparatus according to claim 11, wherein the processing circuitry is also configured to:

indicate pieces of terminal point identification information for identifying terminal points of the core line, at corresponding positions in the region of interest;

receive a contactless input for selecting a specific piece of terminal point identification information from the pieces of terminal point identification information indicated at the corresponding positions in the region of interest;

indicate the first identification information and the second identification information for a core line with a terminal point corresponding to the selected terminal point identification information, in the region of interest;

receive a contactless input related to the first identification information and a contactless input related to the second identification information, a plurality of number of times; and acquire positions of a plurality of points each of which is defined by the contactless input related to the first identification information and the contactless input related to the second identification information, the contactless input having been received a plurality of number of times, and acquire position information of a plane defined by the acquired positions of the points.

13. The medical image processing apparatus according to claim 12, wherein the processing circuitry is configured to indicate the terminal point identification information for a terminal point a distance of which to a branch is equal to or shorter than a predetermined threshold, among the terminal points of the core line of the region of interest.

14. The medical image processing apparatus according to claim 12, wherein the processing circuitry is configured to indicate the terminal point identification information for a terminal point included in a region having a diameter that is equal to or larger than a predetermined threshold, in the region of interest.

15. The medical image processing apparatus according to claim 10, wherein the processing circuitry is further configured to:

set positions along the line of sight in the interior cavity of the region of interest having the tubular structure;

indicate pieces of identification information for identifying the positions along the line of sight in the interior cavity, to corresponding positions in the interior cavity;

receive a contactless input related to the identification information for selecting a position along the line of sight; and acquire a position along the line of sight selected by the contactless input related to the identification information.

16. The medical image processing apparatus according to claim 10, wherein the processing circuitry is configured to provide a rotating view of the medical image, based on a received specific piece of identification information.

17. The medical image processing apparatus according to claim 10, wherein the processing circuitry is also configured to make a measurement using acquired position information.

18. The medical image processing apparatus according to claim 10, wherein the processing circuitry is configured to receive an input via at least one of voice and eye gaze of an operator, as the contactless input.

* * * * *